(12) United States Patent
Shin et al.

(10) Patent No.: US 9,861,329 B2
(45) Date of Patent: *Jan. 9, 2018

(54) X-RAY APPARATUS AND METHOD OF CAPTURING X-RAY IMAGE

(71) Applicant: SAMSUNG ELECTRONICS CO., LTD., Suwon-si (KR)

(72) Inventors: Seung-woo Shin, Yongin-si (KR); Jeong-hwan Kim, Seoul (KR); Do-kwan Oh, Suwon-si (KR); Dong-jae Lee, Hwaseong-si (KR); Sang-chul Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/741,843

(22) Filed: Jun. 17, 2015

(65) Prior Publication Data

US 2015/0282776 A1    Oct. 8, 2015

Related U.S. Application Data

(63) Continuation-in-part of application No. 14/046,227, filed on Oct. 4, 2013, now Pat. No. 9,078,620.

(30) Foreign Application Priority Data

Oct. 11, 2012  (KR) .................. 10-2012-0113042

(51) Int. Cl.
*H05G 1/02* (2006.01)
*A61B 6/00* (2006.01)

(52) U.S. Cl.
CPC .......... *A61B 6/4441* (2013.01); *A61B 6/4435* (2013.01); *A61B 6/4452* (2013.01);
(Continued)

(58) Field of Classification Search
CPC ... A61B 6/4452; A61B 6/5241; A61B 6/4435; H05G 1/02
(Continued)

(56) References Cited

U.S. PATENT DOCUMENTS 4,696,025 A    9/1987  Taylor
5,155,757 A *  10/1992 Sakaniwa ............ A61B 6/4464
                                      378/196
(Continued)

FOREIGN PATENT DOCUMENTS

CN    102551765 A    7/2012
JP    11-290307 A    10/1999
(Continued)

OTHER PUBLICATIONS

Communication dated Mar. 20, 2014 issued by the Korean Intellectual Property Office in counterpart Korean Patent Application No. 10-2012-0113042.
(Continued)

*Primary Examiner* — Courtney Thomas
(74) *Attorney, Agent, or Firm* — Sughrue Mion, PLLC

(57) ABSTRACT

An X-ray apparatus includes: a source configured to emit X-rays to an object; a detector configured to detect the X-rays that have penetrated the object; an arm configured to connect the source to the detector and move centering on a stand fixed to a bottom; a controller configured to control a movement of the arm so that the controller changes a direction of the X-rays, which are radiated to the object, and the arm rotates on the stand to move the detector in a first direction, to obtain images for a plurality of parts of the object; and an image processor configured to obtain the images for the plurality of parts of the object based on the X-rays detected by the detector.

14 Claims, 20 Drawing Sheets

(52) U.S. Cl.
CPC .......... *A61B 6/5205* (2013.01); *A61B 6/5241* (2013.01); *A61B 6/548* (2013.01)

(58) Field of Classification Search
USPC .......................................... 378/62, 193–197
See application file for complete search history.

(56) References Cited

U.S. PATENT DOCUMENTS

| | | | |
|---|---|---|---|
| 5,191,600 | A | 3/1993 | Vincent et al. |
| 6,895,076 | B2 | 5/2005 | Halsmer et al. |
| 6,940,948 | B1 * | 9/2005 | Tretiakov ................. A61B 6/00 378/146 |
| 6,944,265 | B2 | 9/2005 | Warp et al. |
| 7,003,070 | B1 | 2/2006 | Chen et al. |
| 7,142,632 | B2 * | 11/2006 | Atzinger .............. A61B 6/4225 378/196 |
| 7,555,100 | B2 | 6/2009 | Wang et al. |
| 7,785,006 | B2 | 8/2010 | Kim |
| 9,078,620 | B2 * | 7/2015 | Shin ..................... A61B 6/4452 |
| 2007/0269001 | A1 * | 11/2007 | Maschke ......................... 378/38 |
| 2009/0015669 | A1 | 1/2009 | Klingenbeck-Regn |
| 2011/0182408 | A1 * | 7/2011 | Graf et al. ...................... 378/62 |
| 2012/0014512 | A1 | 1/2012 | Kim et al. |
| 2012/0153177 | A1 | 6/2012 | Iwakiri et al. |

FOREIGN PATENT DOCUMENTS

| | | |
|---|---|---|
| JP | 2002-350370 A | 12/2002 |
| JP | 2010-127810 A | 6/2010 |
| JP | 2012-130436 A | 7/2012 |
| KR | 10-2009-0078650 A | 7/2009 |
| WO | 2004/028368 A1 | 4/2004 |

OTHER PUBLICATIONS

Communication dated Nov. 5, 2013 issued by the Korean Intellectual Property Office in counterpart Korean Patent Application No. 10-2012-0113042.

International Search Report and Written Opinion dated Jan. 7, 2014 issued by the International Searching Authority in counterpart Application No. PCT/KR2013/009075 (PCT/ISA/210 & PCT/ISA/237).

Communication dated May 13, 2016, issued by the European Patent Office in counterpart European Application No. 13845333.7.

Communication dated Mar. 27, 2017 by the State Intellectual Property Office of P.R. China in counterpart Chinese Patent Application No. 201310471828.0.

Communication dated Oct. 18, 2017 by the European Patent Office in counterpart European Patent Application No. 13845333.7.

* cited by examiner

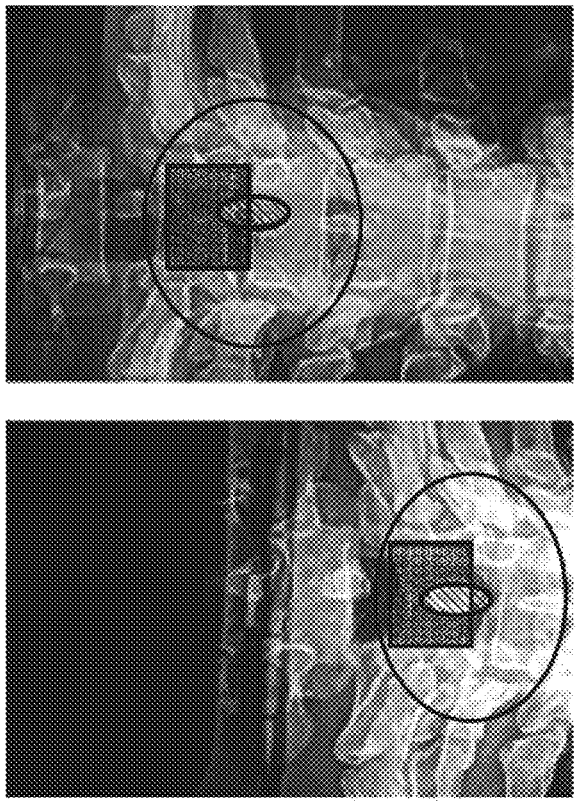
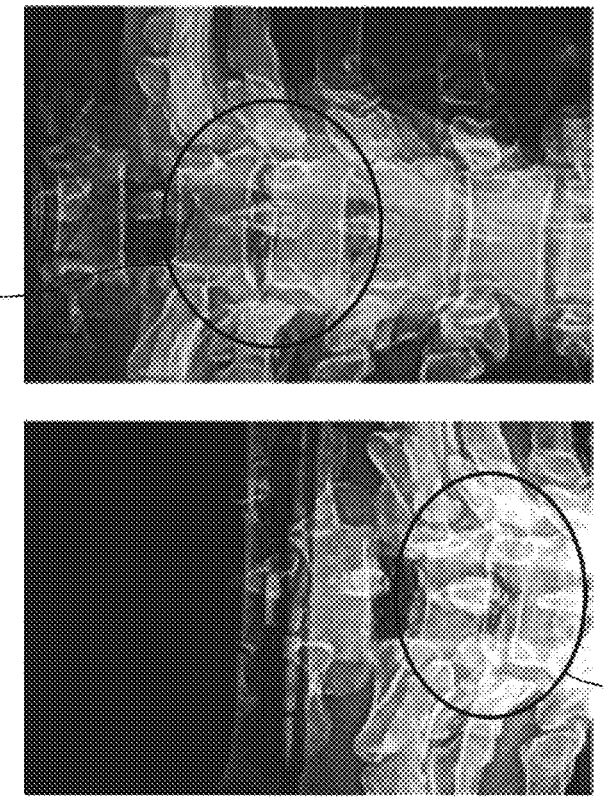

X-RAY APPARATUS AND METHOD OF CAPTURING X-RAY IMAGE

CROSS-REFERENCE TO RELATED PATENT APPLICATIONS

This application is a continuation-in-part of U.S. application Ser. No. 14/046,227, filed Oct. 4, 2013, which claims priority from Korean Patent Application No. 10-2012-0113042, filed Oct. 11, 2012, in the Korean Intellectual Property Office, the disclosures of which are incorporated herein in their entireties by reference.

BACKGROUND

1. Field

Apparatuses and methods consistent with exemplary embodiments relate to capturing an X-ray image by using the X-ray apparatus, and more particularly, to capturing X-ray images by driving the X-ray apparatus.

2. Description of the Related Art

When X-rays penetrate an object, the X-rays attenuate depending on the properties of the object and the distance to the object. An X-ray apparatus may image the internal areas or contents of the human body or objects by using such characteristics, and is widely used in medical imaging and industrial nondestructive testing.

An area of an object, which may be imaged at a time by the X-ray apparatus, may be limited to only a portion of the object based on the desired accuracy and/or resolution. Accordingly, an image stitching technique for obtaining an image having a larger area or higher resolution by combining a plurality of imaging images has been developed. The image stitching technique is generally performed by using computer software, and the irradiation of identical X-rays is needed to obtain an accurate overlap between separate images to be combined.

The X-ray apparatus includes an apparatus for generating X-rays and an apparatus for detecting the X-rays and converting the detected X-rays into an image. Examples of the X-ray apparatus include a ceiling-type X-ray apparatus and a U-arm-type X-ray apparatus.

In the ceiling-type X-ray apparatus, an apparatus for generating X-rays is fixed to a ceiling; thus, providing a wide operating range and easy access to imaging areas of a patient due to the flexibility of operation.

In the U-arm-type X-ray apparatus, an apparatus for generating X-rays and an apparatus for detecting the X-rays are fixed to an arm connected to an arm stand fixed on the ground. The U-arm-type X-ray apparatus has advantages in that an occupation space thereof is small and the price and installation costs thereof are lower, as compared to the ceiling-type X-ray apparatus. However, since an apparatus for generating X-rays and an apparatus for detecting the X-rays are fixed to an arm, the U-arm-type X-ray apparatus has disadvantages in that a degree of freedom is lower, thereby limiting a range of movement, as compared to the ceiling-type X-ray apparatus.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide an X-ray apparatus for minimizing image distortion and obtaining an image for a large area.

According to an aspect of an exemplary embodiment, there is provided an X-ray apparatus including: a source for emitting X-rays to an object; a detector for detecting the X-rays penetrating the object; an arm for connecting the source to the detector and moving the detector up and down according to a rotation of the source; a stand for supporting the arm; and a controller for controlling an imaging for the object by driving the arm.

The controller may control at least one of the source, the detector, and the arm, and may control a straight movement distance of an end of the arm connected to the detector based on an X-ray incident angle of X-rays that are emitted from the source to the detector.

The controller may control the straight movement distance of the end of the arm connected to the detector, in order to perform a second imaging, based on an X-ray incident angle in a first imaging.

The controller may control the arm so that the X-ray incident angle in the first imaging and an X-ray incident angle in the second imaging correspond to each other, in a predetermined area in which a first imaging area corresponding to the first imaging and a second imaging area corresponding to the second imaging overlap with each other.

The controller may control the arm so that the X-ray incident angle in the first imaging and the X-ray incident angle in the second imaging are identical to each other in the predetermined area.

The X-ray apparatus may further include an image processor, wherein the image processor generates a combination image by combining a first image obtained by a first imaging and a second image obtained by a second imaging.

The image processor may generate the combination image by adjusting a magnification or reduction ratio of the first image and a magnification or reduction ratio of the second image based on a distance between the object and the detector.

The detector may maintain a constant angle with respect to the object regardless of the movement of the detector.

The X-ray apparatus may further include: an arm connection unit for connecting the stand to the arm; a source connection unit for connecting the source to the arm; and a detector connection unit for connecting the detector to the arm, wherein the source connection unit and the detector connection unit are positioned below the arm connection unit.

The controller may control the arm to locate the detector at a position that is the same as or above a detector base position which is a position of the detector when an X-ray irradiation angle of the source is perpendicular to an X-ray detection side of the detector.

According to an aspect of an exemplary embodiment, there is provided a method of capturing an X-ray image by using an X-ray apparatus that includes a source, a detector, an arm for connecting the source to the detector, and a stand for supporting the arm, the method including: emitting X-rays to an object; detecting the X-rays penetrating the object; and capturing an X-ray image by driving the arm to move the detector up and down according to a rotation of the source.

The capturing of the X-ray image may include: performing a first imaging of detecting the X-rays penetrating the object by using the detector; controlling at least one of the source, the detector, and the arm, in order to perform a second imaging, based on an incident angle of the X-rays that are emitted from the source to the detector in the first imaging; and performing a second imaging of detecting X-rays penetrating the object by using the detector.

The controlling of the at least one of the source, the detector, and the arm may include controlling a straight movement distance of an end of the arm connected to the detector.

The controlling of the straight movement distance may include controlling the arm so that the X-ray incident angle in the first imaging and an X-ray incident angle in the second imaging correspond to each other, in a predetermined area in which a first imaging area corresponding to the first imaging and a second imaging area corresponding to the second imaging overlap with each other.

The controlling of the straight movement distance may include controlling the arm so that the X-ray incident angle in the first imaging and the X-ray incident angle in the second imaging are identical to each other in the predetermined area.

The method may further include generating a combination image by combining a first image obtained by the first imaging and a second image obtained by the second imaging.

The generating of the combination image may include generating the combination image by adjusting a magnification or reduction ratio of the first image and a magnification or reduction ratio of the second image based on a distance between the object and the detector.

The detector may maintain a constant angle with respect to the object in the capturing of the X-ray image.

The X-ray apparatus may further include: an arm connection unit for connecting the stand to the arm; a source connection unit for connecting the source to the arm; and a detector connection unit for connecting the detector to the arm, wherein the source connection unit and the detector connection unit are positioned below the arm connection unit.

The capturing of the X-ray image may include controlling the arm to locate the detector at a position that is the same as or above a detector base position which is a position of the detector when an X-ray irradiation angle of the source is perpendicular to an X-ray detection side of the detector.

According to an aspect of an exemplary embodiment, there is provided a method of obtaining an X-ray image, the method including: performing a first imaging of emitting X-rays from a source connected to one end of an arm to an object and of detecting the X-rays penetrating the object by using a detector connected to the other end of the arm; moving the detector up and down according to the rotation of the source based on an incident angle of the X-rays that are emitted from the source to the detector; performing a second imaging of emitting X-rays from the source to the object and of detecting the X-rays penetrating the object by using the detector; and obtaining the X-ray image, wherein the obtaining of the X-ray image includes: adjusting a magnification or reduction ratio of a first image obtained in the first imaging and a magnification or reduction ratio of a second image obtained in the second imaging based on a distance between the object and the detector, and generating a combination image by combining the first image and the second image each of which magnification or reduction ratio has been adjusted.

According to an aspect of an exemplary embodiment, there is provided an X-ray apparatus including: a source configured to emit X-rays to an object; a detector configured to detect the X-rays that have penetrated the object; an arm configured to connect the source to the detector and move centering on a stand fixed to a bottom; a controller configured to control a movement of the arm so that the controller changes a direction of X-rays, which are radiated to the object and the arm rotates on the stand to move the detector in a first direction, to obtain images for a plurality of parts of the object.

The controller may control the detector to move the detector in a second direction along the arm so that a distance between the object and the detector is constant, to obtain an image for a second part of the object after obtaining an image for a first part of the object.

The controller may control the arm to move the arm by a first distance in a second direction, centering on the stand, so that a distance between the object and the detector is constant, to obtain an image for a second part of the object after obtaining an image for a first part of the object.

The controller may control the source so that the source moves along the arm by the first distance in a direction opposite to the second direction, to obtain the image for the second part of the object after obtaining the image for the first part of the object.

The controller may control the arm so that the arm moves in the first direction along the stand while rotating on the stand, based on an incident angle of X-rays emitted from the source to the detector, to obtain an image for a second part of the object after obtaining an image for a first part of the object.

The controller may control the arm so that the arm moves in the first direction along the stand while rotating on the stand, so that an X-ray incident angle in a first imaging operation and an X-ray incident angle in a second imaging operation correspond to each other in a predetermined section in which a first part of the object overlaps a second part of the object, to perform the second imaging operation for obtaining an image for a second part of the object after performing the first imaging operation for obtaining an image for a first part of the object.

The controller may control a distance by which the arm moves in the first direction so that an X-ray incident angle in a first imaging operation and an X-ray incident angle in a second imaging operation are identical to each other in a predetermined section.

The controller may control the arm so that the arm moves in the first direction along the stand while rotating by a predetermined angle, so that the detector moves by a predetermined distance in the first direction, to obtain an image for a second part of the object after obtaining an image for a first part of the object, and may control the arm so that the arm moves in the first direction along the stand while rotating by a predetermined angle, so that the detector moves by a predetermined distance in the first direction, to obtain an image for a third part of the object after obtaining the image for the second part of the object.

The image processor may adjust an enlargement or reduction ratio of images for the plurality of parts of the object, based on a distance from the object to the detector which is used when obtaining each of the images of the plurality of parts, and may generate a combination image by combining the images of the plurality of parts.

The controller may control the movement of the arm so that the detector moves from a reference position toward the first direction, to obtain images for the plurality of parts of the object, wherein the reference position is a position of the detector when an X-ray radiation angle of the source for an X-ray detection surface of the detector is 90°.

The controller may control the movement of the arm so that the detector passes a reference position while moving in the first direction, to obtain images of the plurality of parts of the object, wherein the reference position is a position of the detector when an X-ray radiation angle of the source for an X-ray detection surface of the detector is 90°.

According to an aspect of an exemplary embodiment, there is provided a method of capturing an X-ray image by using an X-ray apparatus including a source configured to emit X-rays to an object, a detector configured to detect the X-rays that have penetrated the object, and an arm configured to connect the source to the detector and move centering on a stand fixed to a bottom, the method including: obtaining a first image for a first part of the object, based on X-rays detected by the detector; moving the arm so that a direction of X-rays, which are radiated to the object, is changed and the arm rotates on the stand to move the detector in a first direction; and obtaining a second image for a second part of the object, based on X-rays detected by the detector.

The moving of the arm may include moving the detector in a second direction along the arm so that a distance between the object and the detector when obtaining the first image and a distance between the object and the detector when obtaining the second image are constant.

The moving of the arm may include moving the arm by a first distance in a second direction, centering on the stand, so that a distance between the object and the detector when obtaining the first image and a distance between the object and the detector when obtaining the second image are constant.

The moving of the arm may further include moving the source along the arm by the first distance in a direction opposite to the second direction.

The moving of the arm may include moving the arm so that the arm moves in the first direction along the stand while rotating on the stand, based on an incident angle of X-rays emitted from the source to the detector to obtain the first image and an incident angle of X-rays emitted from the source to the detector to obtain the second image.

The moving of the arm may include moving the arm so that the arm moves in the first direction along the stand while rotating on the stand, so that an X-ray incident angle when obtaining the first image and an X-ray incident angle when obtaining the second image are identical to each other in a predetermined section in which a first part of the object overlaps a second part of the object.

The moving of the arm may include moving the arm by a predetermined distance in the first direction so that the arm moves in the first direction along the stand while rotating on the stand, so that an X-ray incident angle when obtaining the first image and an X-ray incident angle when obtaining the second image correspond to each other in a predetermined section.

The moving of the arm may include moving the arm so that the arm moves in the first direction along the stand while rotating by a predetermined angle, so that the detector moves by a predetermined distance in the first direction, wherein the method further includes moving the arm so that the arm moves in the first direction along the stand while rotating by a predetermined angle, so that the detector moves by a predetermined distance in the first direction, to obtain a third image for a third part of the object after obtaining the second image for the second part of the object.

The method may further include: adjusting an enlargement or reduction ratio of the first and second images, based on a distance from the object to the detector which is used when obtaining each of the first and second images; and generating a combination image by combining the first image with the second image.

The arm may move so that the detector moves from a reference position toward the first direction, to obtain images for a plurality of parts of the object which include the first image and the second image, wherein the reference position is a position of the detector when an X-ray radiation angle of the source for an X-ray detection surface of the detector is 90°.

The arm may move so that the detector passes a reference position while moving in the first direction, to obtain images for a plurality of parts of the object which include the first image and the second image, wherein the reference position is a position of the detector when an X-ray radiation angle of the source for an X-ray detection surface of the detector is 90 °.

According to an X-ray apparatus according to an exemplary embodiment, a method of capturing an X-ray image by using the X-ray apparatus, and a method of obtaining an X-ray image by using the X-ray apparatus, a plurality of images may be stitched without distortion. Accordingly, a highly accurate image for a large area may be obtained.

BRIEF DESCRIPTION OF THE DRAWINGS

The above and/or other aspects will become more apparent by describing in certain exemplary embodiments, with reference to the accompanying attached drawings, in which:

FIGS. 4A, 4B, 4C, and 4D are diagrams illustrating actual images captured according to a stepping method-based imaging;

DETAILED DESCRIPTION

Figure 1:
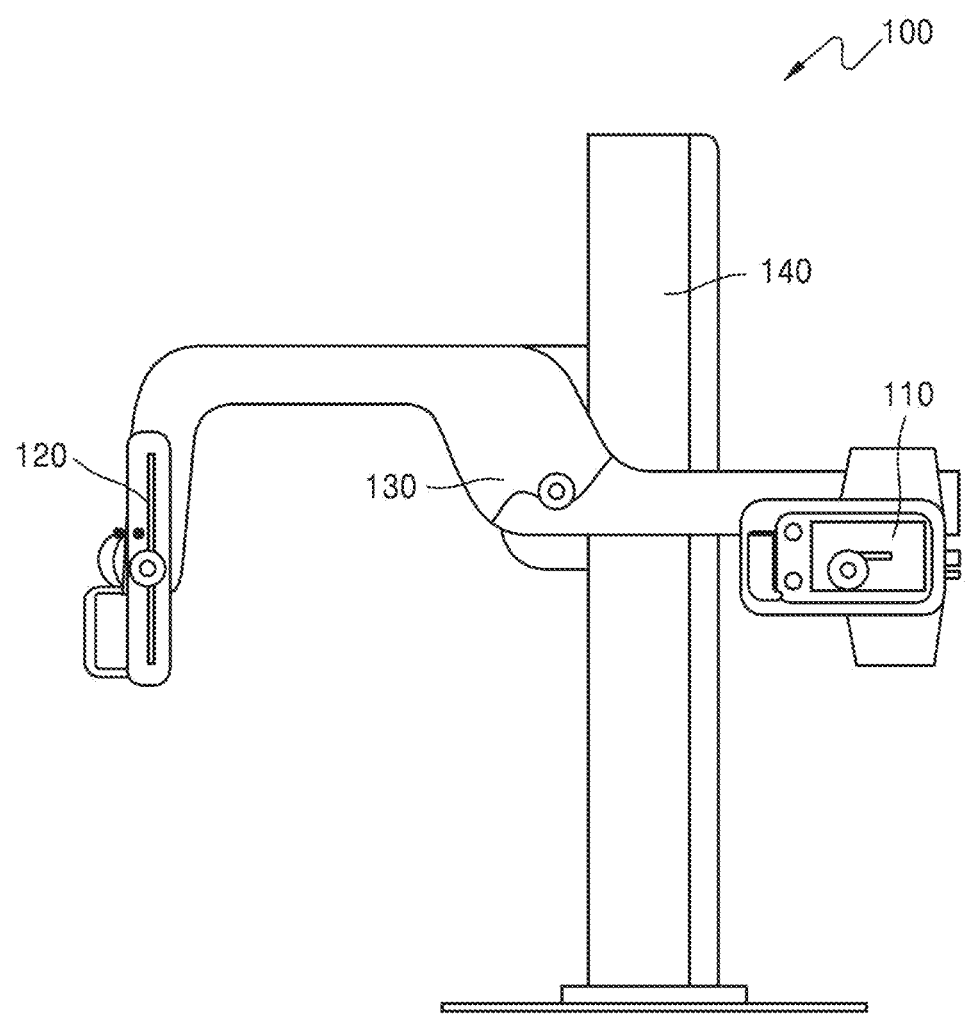
FIG. 1 is a diagram illustrating the structure of an X-ray apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

The terms used in the present specification are used for explaining a certain exemplary embodiments, and are not limiting the present inventive concept. Thus, the expression of singularity in the present specification includes the expression of plurality unless clearly specified otherwise in context. Unless defined otherwise, all terms used herein including technical or scientific terms have the same meanings as those generally understood by those skilled in the art to which the present inventive concept may pertain. The terms as those defined in generally used dictionaries are construed to have meanings matching that in the context of related technology and, unless clearly defined otherwise, are not construed to be ideally or excessively formal.

When a part may "include" a certain element, unless specified otherwise, it is not to be construed to exclude another element but may be construed to further include other elements. The terms such as "~ portion", "~ unit", "~ module", and "~ block" stated in the specification may signify a unit to process at least one function or operation and the unit may be embodied by hardware, software, or a combination of hardware and software. Expressions such as "at least one of," when preceding a list of elements, modify the entire list of elements and do not modify the individual elements of the list.

FIG. 1 is a diagram illustrating the structure of an X-ray apparatus 100. Referring to FIG. 1, the X-ray apparatus 100 includes a source 110 for emitting X-rays to an object and a detector 120 for detecting the X-rays penetrating the object. For example, the X-ray apparatus 100 further includes an arm 130 for connecting the source 110 to the detector 120 and a stand 140 for supporting the arm 130.

Figure 2A:
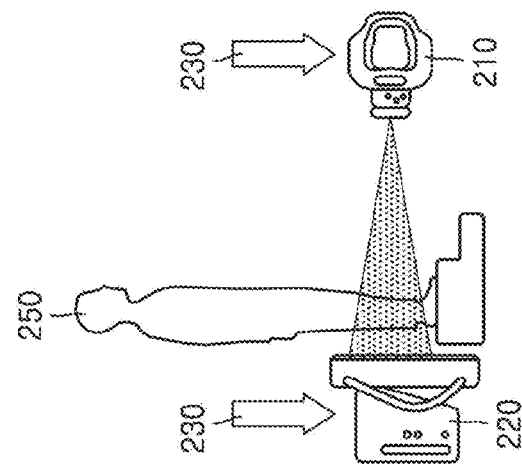
FIGS. 2A, 2B, and 2C are diagrams illustrating a stepping method-based imaging operation of an X-ray apparatus.
Figure 2B:
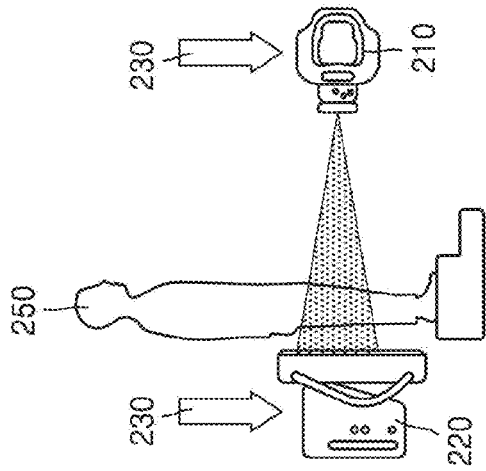
Figure 2C:
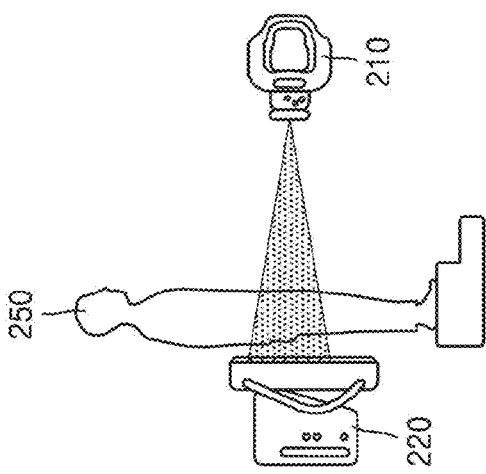

FIGS. 2A through 2C are diagrams illustrating a stepping method imaging operation of the X-ray apparatus 100. The X-ray apparatus 100 illustrated in FIG. 1 may image the object by using a stepping method. The stepping method is a method of capturing an X-ray image of the object while moving the source 110 and the detector 120.

As illustrated in FIG. 2A, according to the stepping method, X-rays are emitted from the source 210 to the detector 220 perpendicularly to an X-ray detection plane of the detector 220. The object 250 is imaged by detecting the X-rays penetrating the object 250. Hereinafter, imaging illustrated in FIG. 2A is referred to as a first imaging, imaging illustrated in FIG. 2B is referred to as a second imaging, and imaging illustrated in FIG. 2C is referred to as a third imaging.

When the first imaging for the object 250 is completed, the second imaging illustrated in FIG. 2B and the third imaging illustrated in FIG. 2C are sequentially performed while moving the detector 220 and the source 210, in a direction 230. During the first, second, and third imaging, an angle of irradiation of the X-rays from the source 210 to the detector 220 and a distance from the source 210 to the detector 220 are maintained constant and only the heights of the source 210 and detector 220 from the ground are changed. According to the stepping method, a large area of an object may be imaged through a plurality of imaging operations. However, image distortion may occur when combining a plurality of images, captured by the stepping method, to make a single image, that is, when performing an image stitching technique.

Figure 3A:
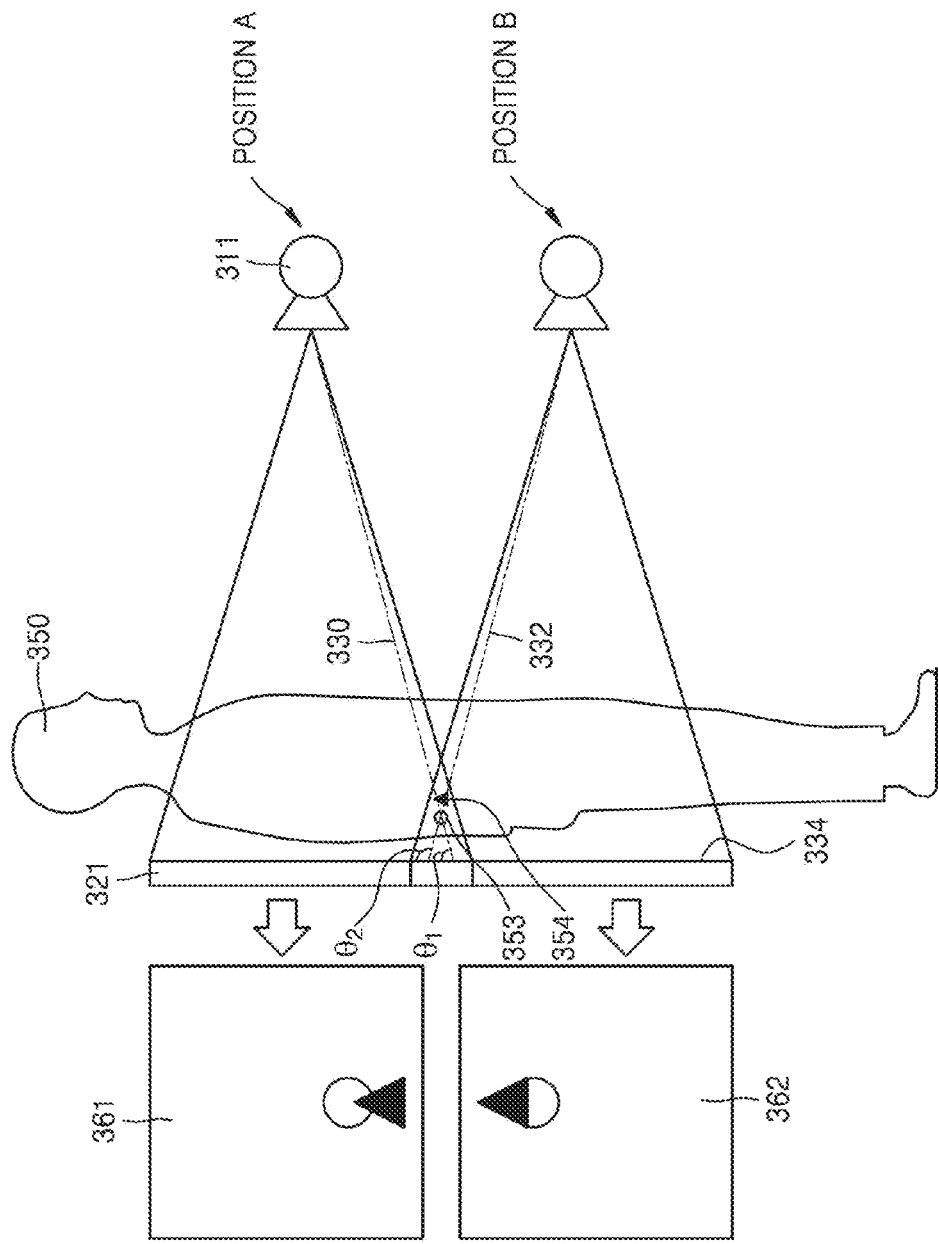
FIGS. 3A and 3B are diagrams for explaining image distortion occurring due to a stepping method-based imaging.
Figure 3B:
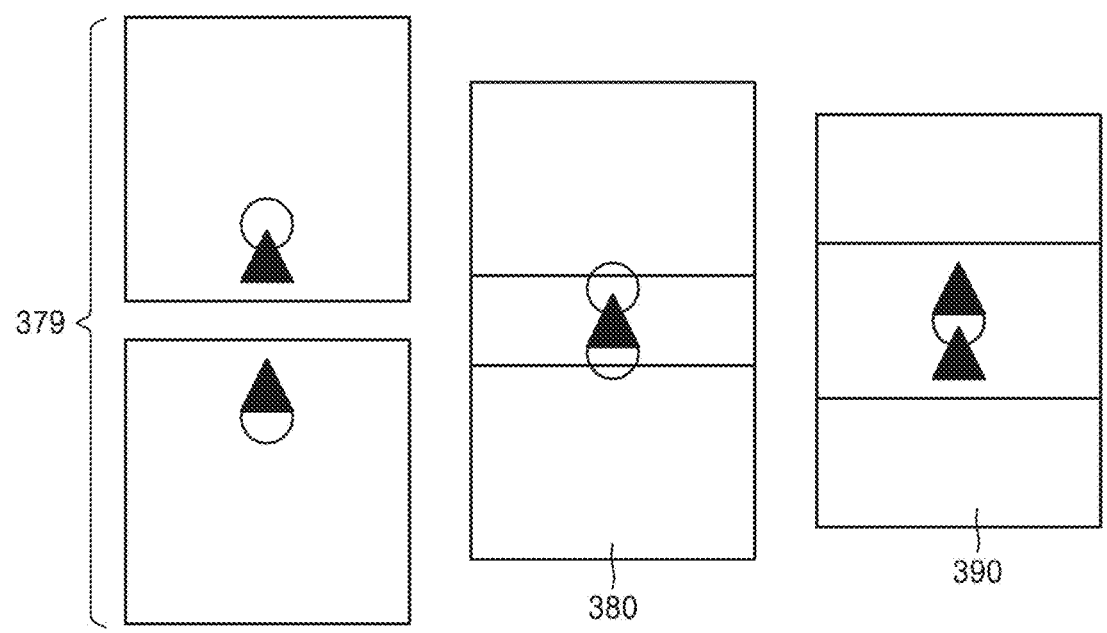

Below, image distortion occurring due to an imaging using the stepping method is described with reference to FIGS. 3A and 3B. FIG. 3A illustrates a first image 361 obtained as a detector 321 detects X-rays penetrating an object 350 after being emitted from a source 311 at a position A. A second image 362 is obtained as a detector 321 detects X-rays penetrating the object 350 after being emitted from a source 311 at a position B.

Referring to FIG. 3A, in the object 350, a first tissue 353 indicated as a circle and a second tissue 354 indicated as a triangle are positioned at the same height. However, relative positions of the first tissue 353 and the second tissue 354, which are observed in the first or second images 361 or 362 obtained by detecting the X-rays penetrating the object 350, are different from the actual case. That is, in the first image 361, an image (a circle) of the first tissue 353 is positioned above an image (a triangle) of the second tissue 353. In the second image 362, an image (a circle) of the first tissue 353 is positioned under an image (a triangle) of the second tissue 354.

Such a difference between the positions of the first tissue 353 and second tissue 354 on the first image 361 and the second image 362 is due to a difference between the incident angle of X-rays that are emitted from the source 311 to the detector 321 at the position A and the incident angle of X-rays that are emitted from the source 311 to the detector 321 at the position B.

The incident angle of X-rays that are emitted from a source to a detector is an angle between the X-rays emitted from the source and an X-ray detection plane 334 of the detector. Accordingly, the incident angles of X-rays that are incident on each point of the X-ray detection plane of the detector are different from each other. Referring to FIG. 3A, an incident angle $\Theta_1$ is an angle between the direction of X-rays 330 penetrating the first and second tissues 353 and 354 of the object 350 after the X-rays are emitted from the source 311 at the position A and an X-ray detection plane of the detector 321. An incident angle $\Theta_2$ is an angle between the direction of X-rays 332 penetrating the first and second tissues 353 and 354 of the object 350 after the X-rays are emitted from the source at the position B and an X-ray detection plane of the detector 322. In this case, an incident angle of X-rays penetrating the first and second tissues 353 and 354 is $\Theta_1$ for the first image 361 and $\Theta_2$ for the second image 362, and $\Theta_1$ and $\Theta_2$ are different from each other. Thus, relative positions of the first tissue 353 and the second tissue 354, which are observed in the first image 361, are different from those which are observed in the second image 362.

Accordingly, due to the difference between the positions of the first tissue 353 and second tissue 354 on the first image 361 and the second image 362, image distortion occurs when making a single image by combining the first image 361 and the second image 361, that is, when performing an image stitching.

The image distortion occurring due to the combination of the first image 361 and the second image 362 is described with reference to FIG. 3B. An image 379 shows a state before the first image 361 and the second image 362 are not combined. An image 380 shows an image obtained by combining the first image 361 with the second image 362 based on the image of the second tissue 354. An image 390 shows an image obtained by combining the first image 361 with the second image 362 based on the image of the first tissue 353. Referring to the image 380 and the image 390, image distortion shown as a double image of the first tissue 353 or second tissue 354 occurs in an area in which the first image 361 and the second image 362 overlap with each other.

FIGS. 4A through 4D are diagrams illustrating actual images captured according to the stepping method-based imaging of the X-ray apparatus 100. FIG. 4A illustrates an image captured by imaging a predetermined area of an object. FIG. 4B illustrates an image captured by imaging an area different from the predetermined area of the object. Circles 401 and 402 indicate an area of the object, which is repeatedly imaged. Referring to the circle 401 of FIG. 4A and the circle 402 of FIG. 4B, an image of the circle 401 and an image of the circle 402 are not matched with each other although the same area of the object has been imaged.

Referring to FIGS. 4C and 4D which schematically illustrate FIGS. 4A and 4B, such an image mismatching is easily understood. A position relation between a first tissue indicated by dots and a second tissue indicated by slashes, illustrated in FIG. 4C, is different from that illustrated in FIG. 4D. Accordingly, image distortion occurs when stitching two images, that is, the image illustrated in FIG. 4C and the image illustrated in FIG. 4D. Thus, an exemplary embodiment provides an X-ray apparatus that may minimize image distortion occurring when performing a stitching to obtain an image for a large area. Also, the present invention provides a method of capturing an X-ray image by using the X-ray apparatus.

Figure 5:
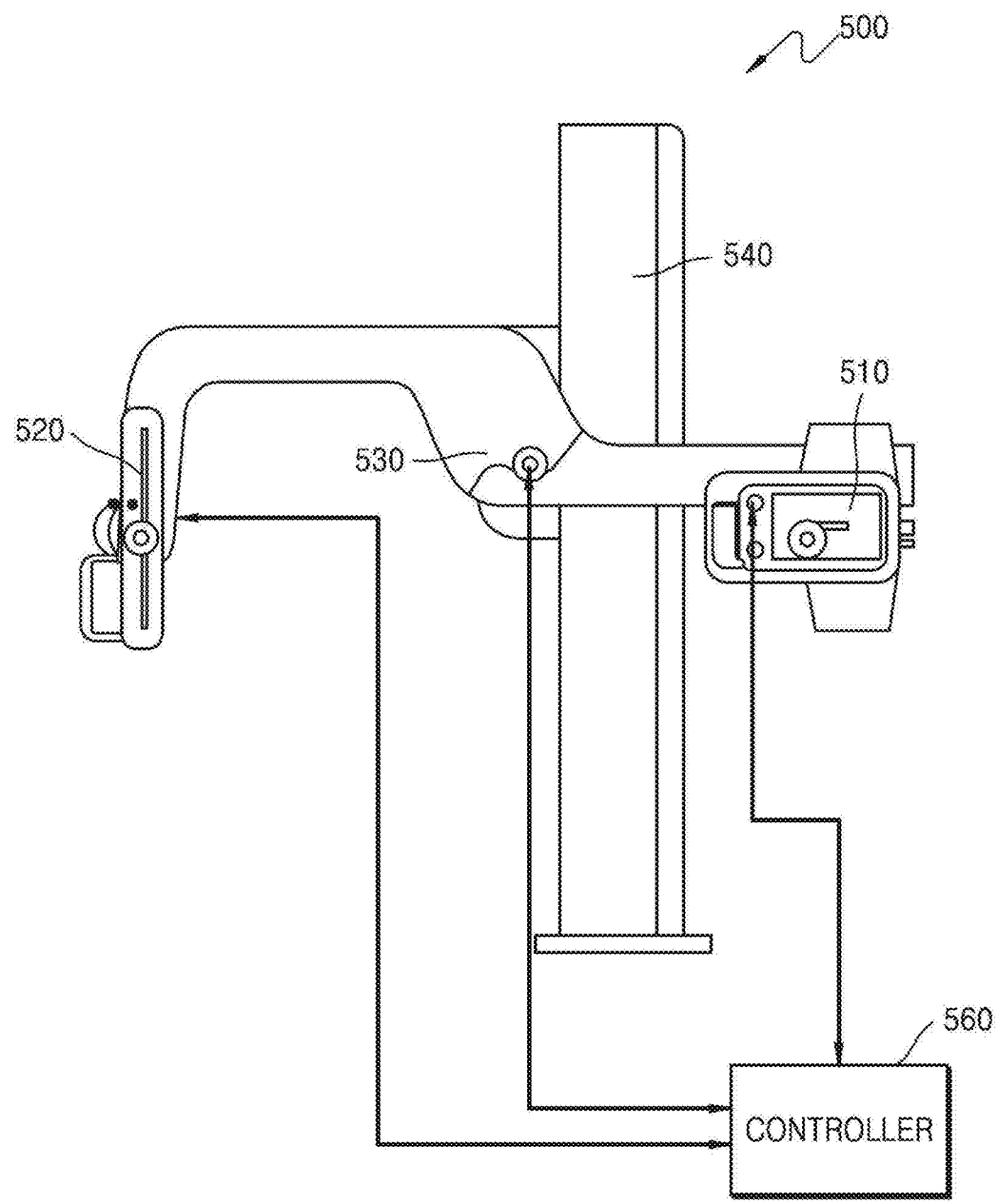
FIG. 5 is a diagram illustrating an X-ray apparatus according to an exemplary embodiment.

FIG. 5 is a diagram illustrating an X-ray apparatus 500 according to an exemplary embodiment.

Referring to FIG. 5, the X-ray apparatus 500 includes a source 510, a detector 520, an arm 530, a stand 540, and a controller 560. The source 510 emits X-rays to an object, and the detector 520 detects the X-rays penetrating the object. The arm 530 connects the source 510 to the detector 520, and may move about the stand 540 which is fixed at the bottom side. The arm 530 may move the detector 520 up and down by rotating on the stand 540 and moving along the stand 540. Also, the arm 530 may move the detector 520 up and down according to the rotation of the source 510. The detector 520 may maintain a constant angle with respect to the object regardless of up and down movement. The stand 540 supports the arm 530, and the controller 560 controls the imaging of the object by driving the arm 530. The arm 530 may change a direction of X-rays which are radiated to an object by the source 510.

The controller 560 may control the movement of the arm 530 to obtain images for a plurality of parts of an object. The controller 560 may control the arm 530 so that a direction of X-rays that are radiated to the object by the source 510 is changed and the arm 530 rotates on the stand 540 to move the detector 520 in a first direction.

The controller 560 controls at least one of the source 510, the detector 520, and the arm 530, and may control the arm 530 connected to the detector 520, in order to perform a second imaging, based on an incident angle of X-rays that are emitted from the source 510 to the detector 520 during a first imaging. In this case, the arm 530 may be controlled to be rotated on the stand 540 or to be moved up and down, and the controller 560 may move the detector 520 by controlling a straight movement distance of an end of the arm 530 connected to the detector 520. In detail, the controller 560 may control the straight movement distance of the end of the arm 530 connected to the detector 520, and may vertically move the detector 520 according to the straight movement distance. The controller 560 may move the detector 520 by a predetermined distance in a predetermined direction by controlling the arm 530 so that the arm 530 moves in the predetermined direction while rotating on the stand 540.

Controlling the arm 520 based on an X-ray incident angle may be controlling the arm 520 so that an X-ray incident angle in a first imaging and an X-ray incident angle in a second imaging correspond to each other, in a predetermined area in which a first imaging area corresponding to the first imaging and a second imaging area corresponding to the second imaging overlap with each other. For example, the controlling of the arm 520 based on an X-ray incident angle may be controlling the arm 520 so that in the predetermined area, a difference between the X-ray incident angle in the first imaging and the X-ray incident angle in the second imaging is within a predetermined acceptable range. The predetermined acceptable range means a difference between the X-ray incident angle in the first imaging and the X-ray incident angle in the second imaging, which allows at least two tissue areas positioned at the same point (for example, the first and second tissues 353 and 354 illustrated in FIG. 3A) to be shown to be positioned at the same point in the first imaging area (for example, the first image 361 of FIG. 3A) and the second imaging area (for example, the second image 362 of FIG. 3A). The predetermined acceptable range may mean a difference between incident angles of X-rays that are incident toward an overlapping area included in continuous imaging areas in common, in which it is previously determined that distortion does not occur when stitching a plurality of images. The predetermined acceptable range may be a value predetermined as a default value or a value set by a user. For example, the controlling of the arm 520 based on an X-ray incident angle may be controlling the arm 520 so that the X-ray incident angle in the first imaging and the X-ray incident angle in the second imaging are identical to each other in a predetermined area.

Figure 6:
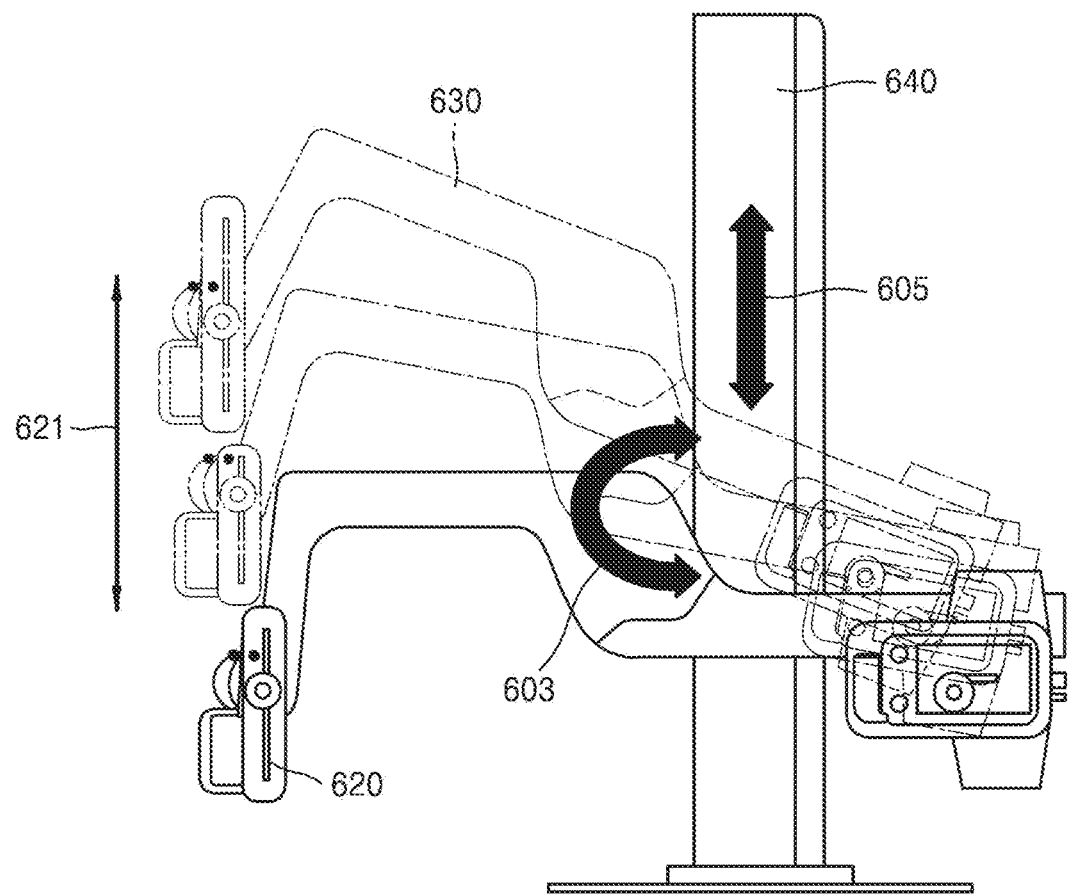
FIG. 6 is a diagram illustrating an operation of an X-ray apparatus according to an exemplary embodiment.

FIG. 6 is a diagram illustrating an operation of the X-ray apparatus according to an exemplary embodiment. An arm 630 and stand 640 illustrated in FIG. 6 correspond to the arm 530 and stand 540 illustrated in FIG. 5, and thus, descriptions overlapping with those of FIG. 5 are not repeated.

As illustrated in FIG. 6, the arm 630 may rotate as indicated by an arrow 603 with respect to the stand 640, and may also move up and down as indicated by an arrow 605. For example, the detector 620 positioned in the end of the arm 630 may move straight as indicated by an arrow 621 to correspond to the rotation or to the up and down movement of the arm 630.

Figure 7A:
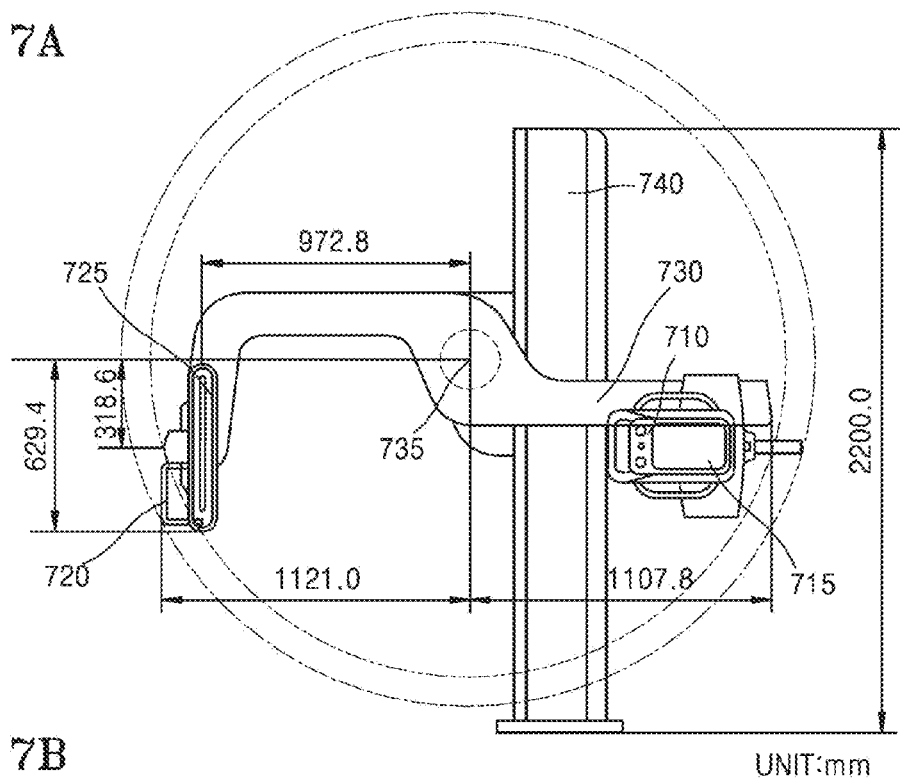
FIGS. 7A and 7B are diagrams for explaining a simulation imaging using an X-ray apparatus according to an exemplary embodiment.
Figure 7B:
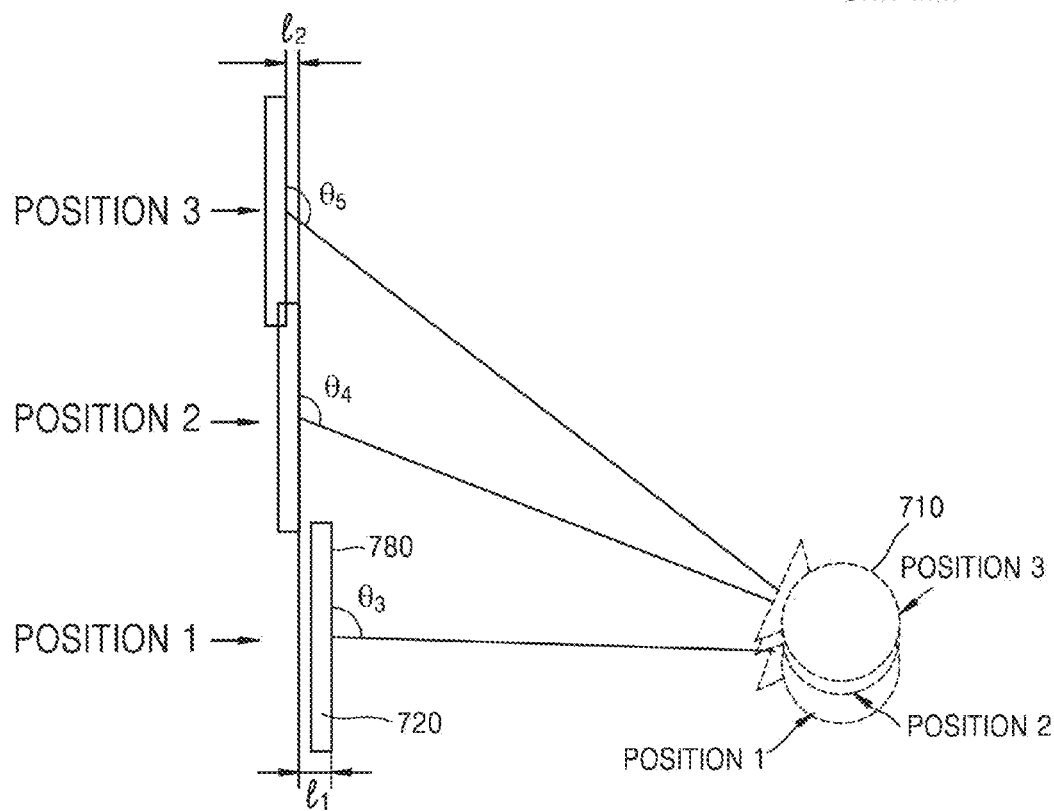

FIGS. 7A and 7B are diagrams for explaining a simulation imaging using the X-ray apparatus according to an exemplary embodiment. The X-ray apparatus illustrated in FIG. 7A is used for simulation. The X-ray apparatus of FIG. 7A includes a source 710, a detector 720, an arm 730, a stand 740, and a controller (not shown). For example, the X-ray apparatus of FIG. 7A may further include an arm connection unit 735 for connecting the stand 740 to the arm 730, a source connection unit 715 for connecting the source 710 to the arm 730, and a detector connection unit 725 for connecting the detector 720 to the arm 730. The source connection unit 715 may be the center about which the source 710 rotates, the detector connection unit 725 may be the center about which the detector moves, and the arm connection unit 735 may be the center about which the arm 730 rotates and/or moves. For example, the arm connection unit 735 may include a point which may be a center point about which the arm 730 rotates and/or moves.

In order to stably drive the arm 730, the detector 720 and the source 710 are positioned below the arm 730 in consideration of the weight of the detector 720 and source 710. That is, the source connection unit 715 and the detector connection unit 725 may be positioned below the arm connection unit 735. For example, an imaging of an object may be performed by controlling the arm 730 to locate the detector 720 above a base position or a first position. The base position of the detector 720 is a position of the detector 720 when an X-ray irradiation angle of the source 710 is perpendicular to an X-ray detection plane of the detector 720. The X-ray irradiation angle of the source 710 is an angle between the center point of the X-ray detection plane of the detector 720 and the source 710.

FIG. 7A illustrates the X-ray apparatus in which the detector 720 is positioned at the base position. As illustrated in FIG. 7A, the source connection unit 715 and the detector connection unit 725 are positioned below the arm connection unit 735, and an object may be imaged by controlling the arm 730 to locate the detector 720 above the base position, to alleviate a possibility of a collision which may occur as a distance between the detector 720 and the object may rapidly shorten when the detector 720 moves below the base position while the arm 730 rotates. For example, as illustrated in FIG. 7B, the position 1 is the base position and the arm 730 may be controlled to locate the detector 720 at a position 1 or above the position 1 (for example, at a position 2 or at a position 3).

Figure 8:
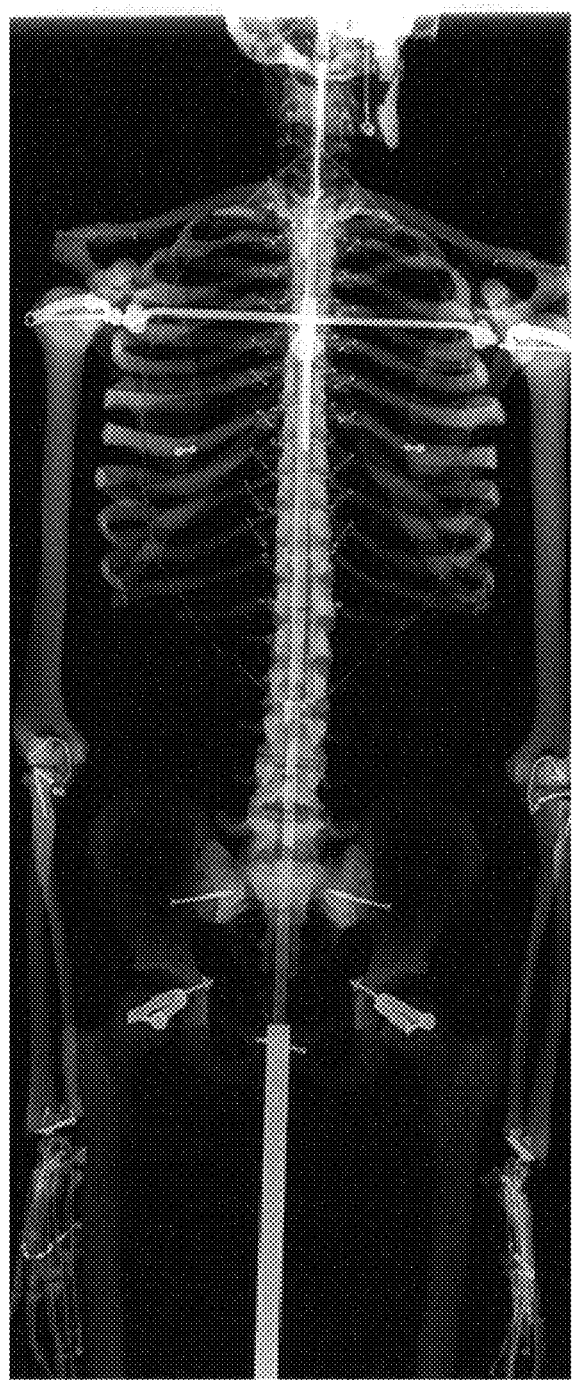
FIG. 8 illustrates a simulation result image obtained using an X-ray apparatus according to an exemplary embodiment.

FIG. 7B is a diagram schematically illustrating an operation of the X-ray apparatus of FIG. 7A, used for simulation. The X-ray apparatus controls the arm 730 to move the detector 720 from the position 1 to the position 2 and from the position 2 to the position 3 while overlapping the positions with each other by approximately 5 cm. FIG. 8 illustrates a result obtained through the stitching of an image captured by moving the detector 720 upward while increasing an angle of the arm 730 by 12°. The angle of the arm 730 is an angle between the arm 730 and the X-ray detection plane 780 of the detector 720. In the current simulation, the angle of the arm 730 is controlled so as to coincide with the X-ray irradiation angle of the source 710. $\Theta_3$ indicates the angle of the arm 730 in an imaging performed in the position 1, $\Theta_4$ indicates the angle of the arm 730 in an imaging performed in the position 2, and $\Theta_5$ indicates the angle of the arm 730 in an imaging performed in the position 3. In FIG. 7B, the arm 730 is not illustrated. The detector 720 may move so that a height from the ground varies. In the current simulation, detailed driving coordinates of the X-ray apparatus are indicated in Table 1.

TABLE 1

| Position | Angle of Arm (°) | Height of Arm (mm) | Detector Push (mm) |
|---|---|---|---|
| 1 | 90 | 0 | 0 |
| 2 | 102 | 165 | 44 |
| 3 | 114 | 320 | 4 |

As illustrated in Table 1, an imaging was performed while increasing the angle of the arm 730 by 12° and increasing the height of the arm 730, based on the position 1. When the arm 730 is controlled as illustrated in Table 1, a difference between an X-ray incident angle in a previous imaging and an X-ray incident angle in a next imaging is placed within the range of ±0.3° in a predetermined area in which imaging areas of the detector 720 overlap with each other.

The detector 720 moves away from the object as the angle and height of the arm 730 are controlled, and the extent that the detector 720 is pushed is shown in Table 1. Referring to FIG. 7B, the detector push generated when the detector 720 moves from the position 1 to the position 2 is illustrated as $l_1$, and the detector push generated when the detector 720 moves from the position 2 to the position 3 is illustrated as $l_2$. The image of the object that is detected by the detector 720 is magnified when the object becomes more distant from the detector 720, and is reduced when the object gets closer to the detector 720. Accordingly, the X-ray apparatus may further include an image processor (not shown) that adjusts a magnification or reduction ratio of the image of the object based on a distance between the object and the detector 720 and generates a combination image based on the adjusted magnification or reduction ratio. The image processor is described with reference to FIG. 9 below.

FIG. 8 is a diagram illustrating a simulation result image obtained using the X-ray apparatus illustrated in FIG. 7A. As can be observed from the simulation result image of FIG. 8, the images captured according to an exemplary embodiment exhibit an undistorted stitching of separate overlapping images. A seamless image for a large area of the object is shown in FIG. 8.

Figure 9:
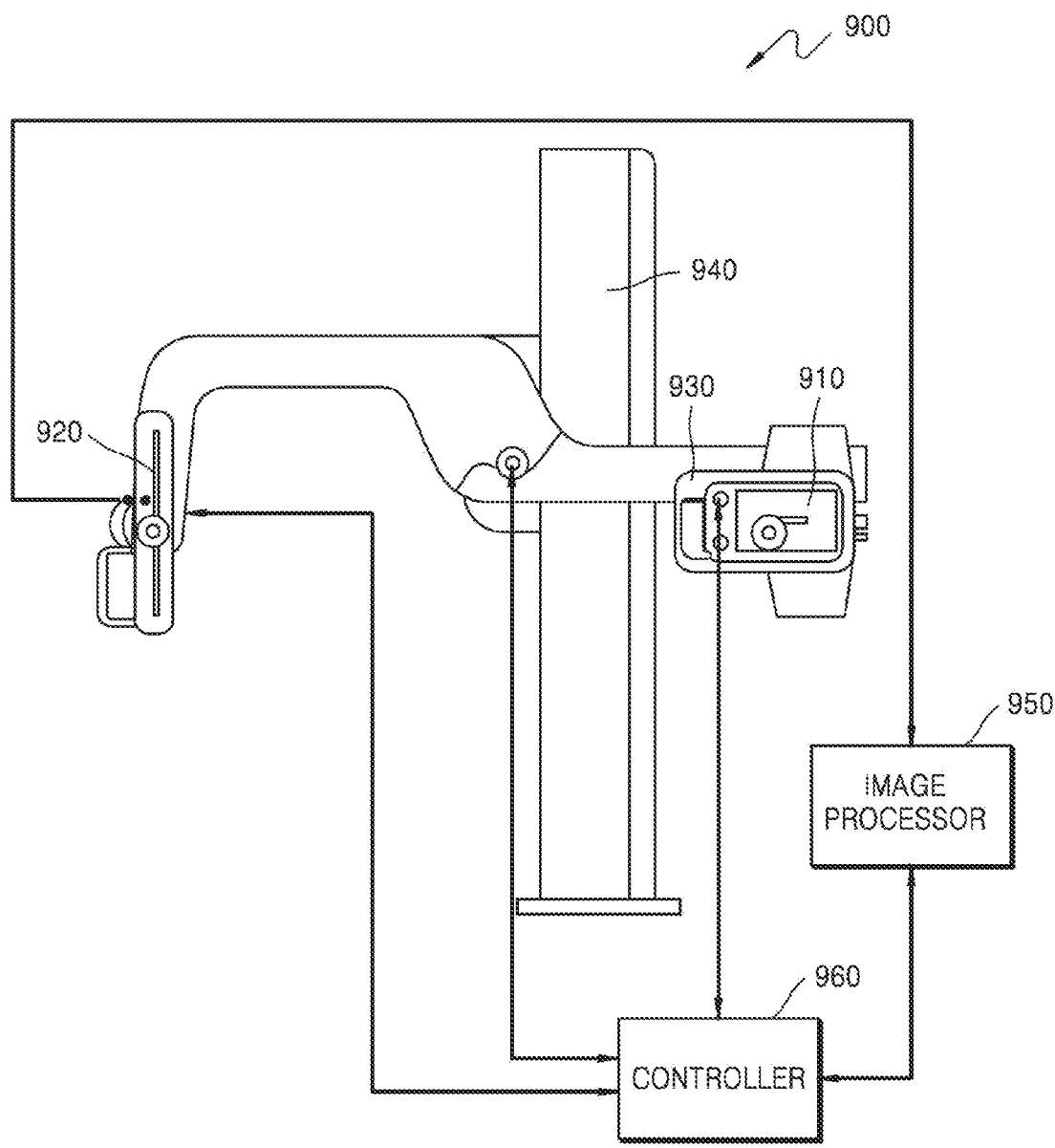
FIG. 9 is a diagram illustrating an X-ray apparatus according to an exemplary embodiment.

FIG. 9 is a diagram illustrating an X-ray apparatus 900 according to an exemplary embodiment.

Referring to FIG. 9, the X-ray apparatus 900 includes a source 910, a detector 920, an arm 930, a stand 940, a controller 960, and an image processor 950. The source 910, the detector 920, the arm 930, the stand 940, and the controller 960, illustrated in FIG. 9, correspond to the source 510, the detector 520, the arm 530, the stand 540, and the controller 560, illustrated in FIG. 5, respectively. Thus, descriptions overlapping with those of FIG. 5 are not repeated.

The image processor 950 may obtain images for a plurality of parts of an object based on X-rays detected by the detector 520. The image processor 950 may generate a combination image by combining images obtained by the detector 920 that detects X-rays penetrating an object. For example, the image processor 950 may adjust a magnification or reduction ratio of the image of the object based on a distance between the object and the detector 920 and may generate the combination image based on the adjusted magnification or reduction ratio.

Figure 10:
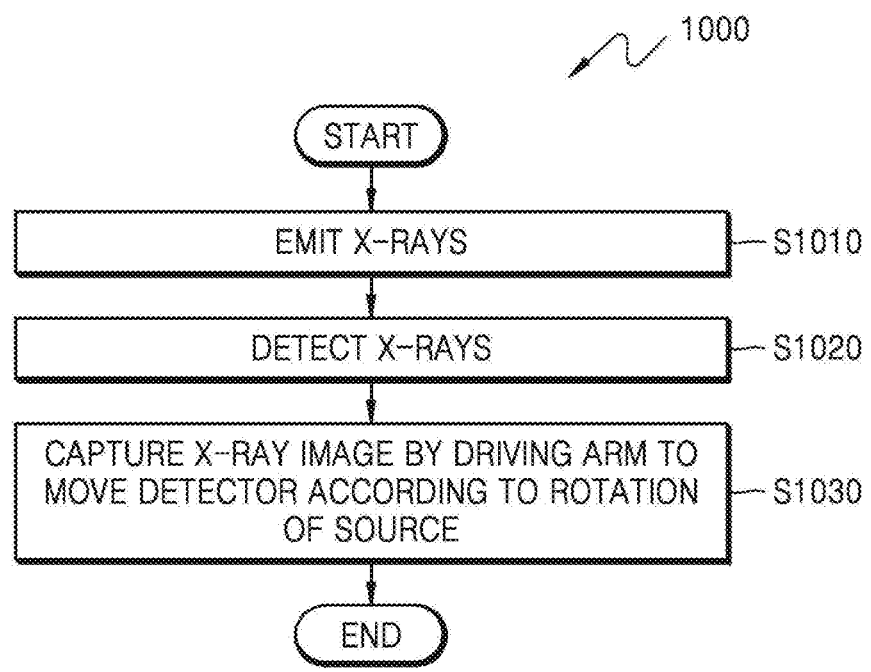
FIG. 10 is a flowchart illustrating a method of capturing an X-ray image, according to an exemplary embodiment.

FIG. 10 is a flowchart illustrating a method 1000 of capturing an X-ray image, according to an exemplary embodiment.

The method 1000 of capturing an X-ray image may be performed by the X-ray apparatus 500 described with reference to FIG. 5. Operations of the method 1000 of capturing an X-ray image are substantially the same as the operations of the X-ray apparatus 500. Accordingly, descriptions overlapping with those of FIG. 5 are not repeated.

Referring to FIG. 10, the X-ray apparatus 500 performs an operation of emitting X-rays to an object (operation S1010), an operation of detecting the X-rays penetrating the object (operation S1020), and an operation of capturing an X-ray image by driving the arm 530 to move the detector 520 up and down according to a rotation of the source 510 (operation S1030). The operation S1010 of emitting the X-rays may be performed by the source 510, the operation S1020 of detecting the X-rays may be performed by the detector 520, and the operation S1030 of capturing the X-ray image may be performed by the controller 560.

Figure 11:
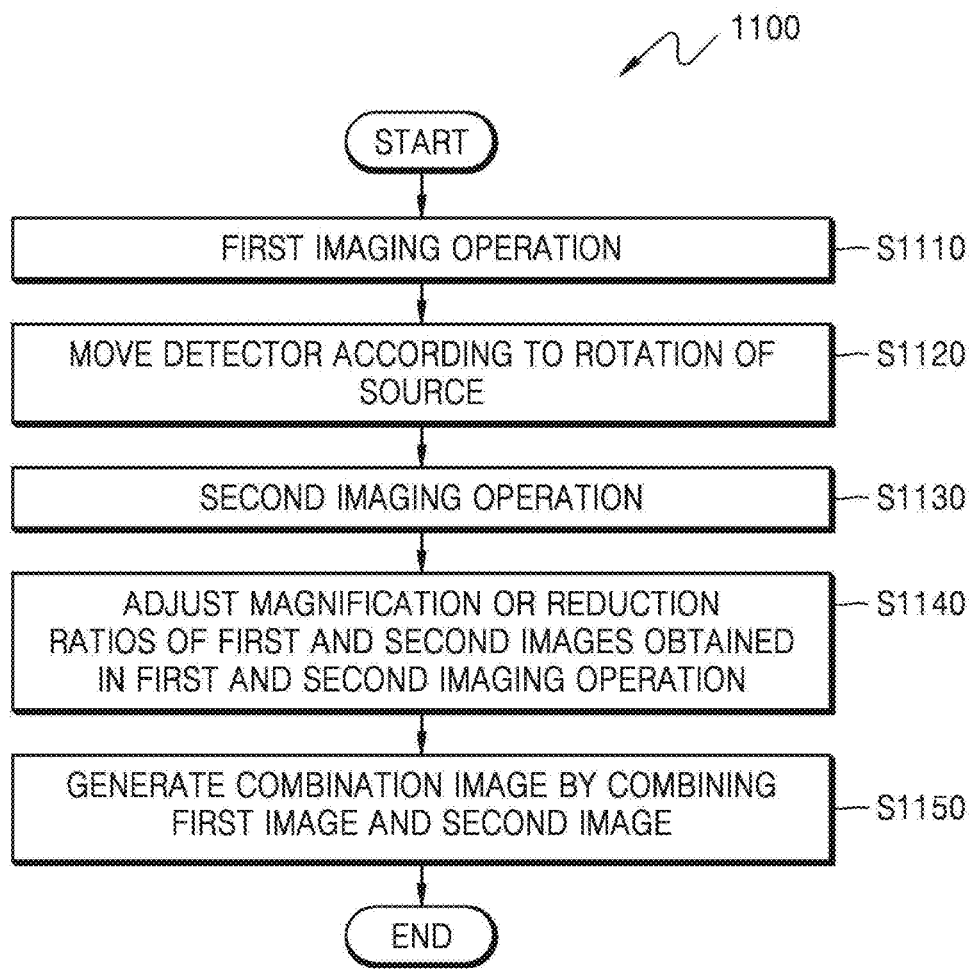
FIG. 11 is a flowchart illustrating a method of obtaining an X-ray image, according to an exemplary embodiment.

FIG. 11 is a flowchart illustrating a method 1100 of obtaining an X-ray image, according to an exemplary embodiment.

The method 1100 of obtaining an X-ray image may be performed by the X-ray apparatus 900 described with reference to FIG. 9. Operations of the method 1100 of obtaining an X-ray image are substantially the same as the operations of the X-ray apparatus 900. Accordingly, descriptions overlapping with those of FIG. 9 are not repeated.

Referring to FIG. 11, the X-ray apparatus 900 performs a first imaging operation of emitting X-rays from the source 910 to an object and of detecting the X-rays penetrating the object by using the detector 920 (operation S1110), an operation of moving the detector 920 up and down according to the rotation of the source 910 based on an incident angle of X-rays that are emitted from the source 910 to the detector 920 (operation S1120), and a second imaging operation of emitting X-rays from the source 910 to the object and of detecting the X-rays penetrating the object by using the detector 920 (operation S1130). For example, the X-ray apparatus 900 performs an operation of adjusting a magnification or reduction ratio of a first image obtained in the first imaging operation and a magnification or reduction ratio of a second image obtained in the second imaging operation based on a distance between the object and the detector 920 (operation S1140), and an image obtaining operation of generating a combination image by combining the first image and the second image each of which magnification or reduction ratio has been adjusted (operation S1150).

Figure 12:
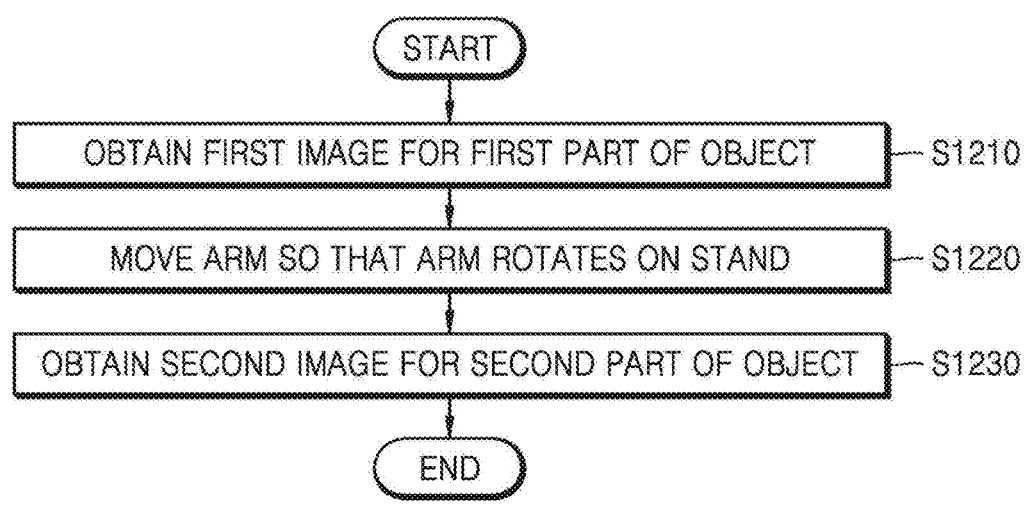
FIG. 12 is a flowchart illustrating a method of capturing an X-ray image, according to an exemplary embodiment.

FIG. 12 is a flowchart illustrating a method of capturing an X-ray image, according to an exemplary embodiment.

The X-ray image capturing method illustrated in FIG. 12 may be performed by the X-ray apparatus 900 described with reference to FIG. 9. Operations of the X-ray image capturing method illustrated in FIG. 12 may be respectively performed by components of the X-ray apparatus 900, and thus, descriptions overlapping with those of FIG. 9 are not repeated.

The X-ray apparatus 900 may obtain a plurality of image for a plurality of parts of an object. FIG. 12 illustrates, as an example, a case in which the X-ray apparatus 900 performs a second imaging operation for obtaining a second image for a second part of the object after performing a first imaging operation for obtaining a first image for a first part of the object.

In operation S1210, the X-ray apparatus 900 may obtain a first image for a first part of an object, based on X-rays detected by the detector 920.

The X-ray apparatus 900 may generate a composite image for a larger area of the object by obtaining a plurality of images for a plurality of imaging areas of the object and composing the obtained images.

A user may designate an imaging start area and an imaging end area of the object by moving or rotate the source 910. The x-ray apparatus 900 may determine an area from the imaging start area to the imaging end area as an imaging section. The controller 960 of the X-ray apparatus 900 may determine how many images it will capture in the image section, and may determine a width of an area in which each imaging area overlaps an imaging area to be imaged next. The controller 960 may control the X-ray apparatus so that each of the plurality of imaging areas overlaps another imaging area.

The X-ray apparatus 900 may obtain a first image for a first part of an object which corresponds to one imaging area selected from a plurality of imaging areas included in an imaging section. The X-ray apparatus 900 may emit X-rays toward the first part of the object, detect the X-rays penetrating the first part of the object, and obtain the first image based on the detected X-rays.

In operation S1220, the X-ray apparatus 900 may change a direction of X-rays that are radiated to the object by the source 910 and move the arm 930 so that the arm 930 rotates on the stand 940 to move the detector 920 in a first direction. For example, when the X-ray apparatus 900 images a standing human body, the X-ray apparatus 900 may obtain images for a plurality of parts of the standing human body while moving the detector 920 up and down.

The X-ray apparatus 900 may divide an object into a plurality of parts in the first direction and obtain a plurality of images for the plurality of parts of the object. In order to obtain the plurality of images for the plurality of parts of the object, the X-ray apparatus 900 may move the detector 920 in the first direction and change a direction of X-rays that are radiated to the object by the source 910.

In order to obtain the plurality of images for the plurality of parts of the object, the X-ray apparatus 900 may rotate the arm 930 by a predetermined angle so that the detector 920 moves by a predetermined distance in the first direction. For example, the X-ray apparatus 900 may rotate the arm 930 by a predetermined angle so that the detector 920 moves by a predetermined distance in the first direction, to perform a second imaging operation after performing a first imaging operation. Also, the X-ray apparatus 900 may rotate the arm 930 by a predetermined angle so that the detector 920 moves by a predetermined distance in the first direction, to perform a next imaging after performing the second imaging operation.

When the detector 920 moves by a predetermined distance in the first direction and the arm 930 is rotated by a predetermined angle, to perform the second imaging operation, the X-ray apparatus 900 may control a moving distance that the arm 930 moves in the first direction along the stand 940, based on an incident angle of X-rays emitted to the detector 920 by the source 910 during the first imaging operation.

More specifically, the X-ray apparatus 900 may control a rotation angle that the arm 930 rotates on the stand 940 and a moving distance that the arm 930 moves along the stand 940, based on an incident angle of X-rays in the first imaging operation and an incident angle of X-rays in the second imaging operation. The X-ray apparatus 900 may move the arm 930 so that an incident angle of X-rays which are used when obtaining a second image corresponds to an incident angle of X-rays that are used when obtaining a first image, in a predetermined section in which a second part of an object overlaps a first part of the object. For example, the X-ray apparatus 900 may move the arm 930 in the first direction so that an incident angle of X-rays which are used when obtaining a second image is identical to an incident angle of X-rays that are used when obtaining a first image, in a predetermined section.

In operation S1230, the X-ray apparatus 900 may obtain a second image for a second part of the object, based on X-rays detected by the detector 920.

As described above, the X-ray apparatus 900 may support distortionless stitching using captured images by controlling a rotation angle and a moving distance of the arm 930 in consideration of incident angles of X-rays that are incident on an overlapping area between adjacent imaging areas.

Figure 13:
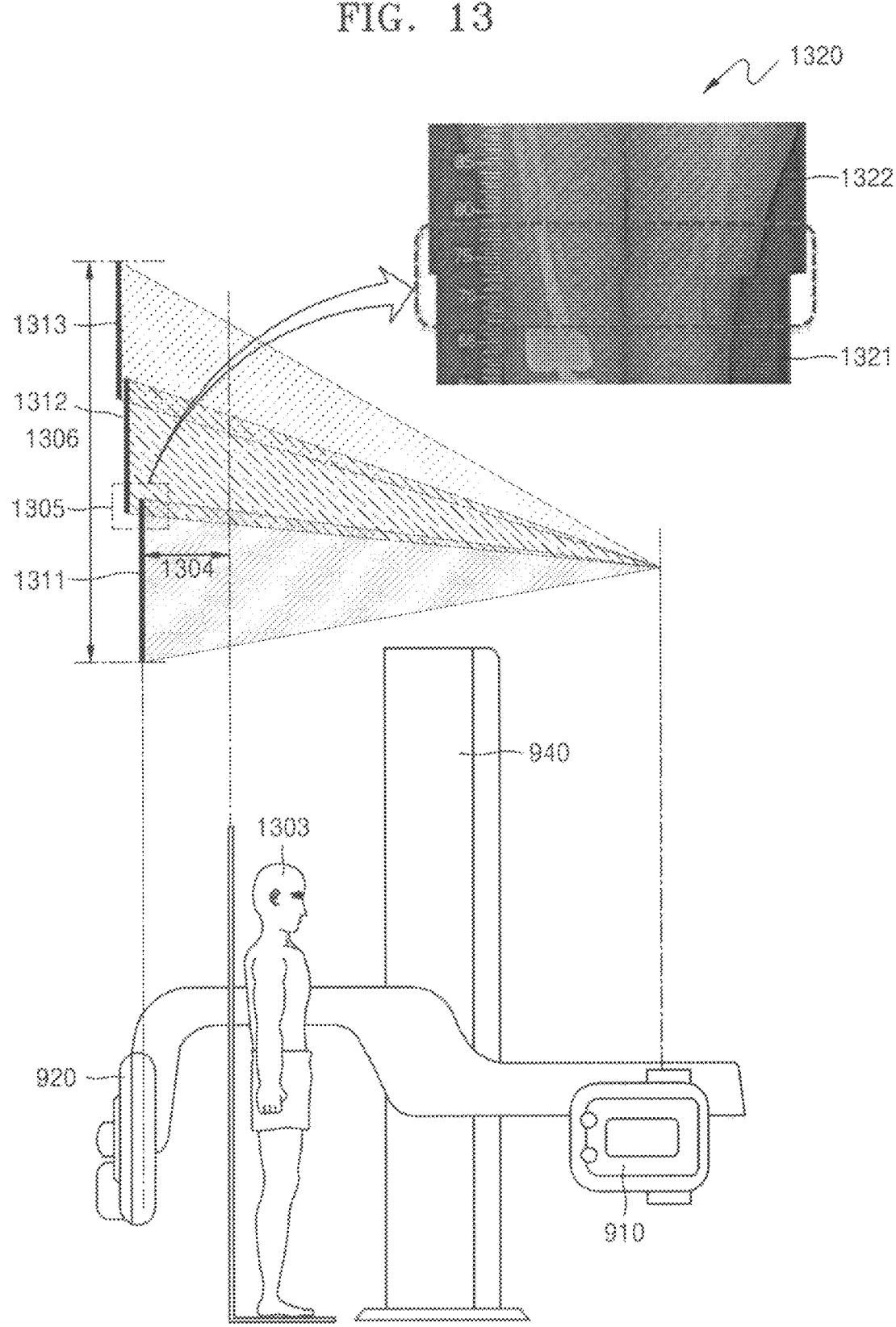
FIG. 13 is a diagram illustrating a method in which the X-ray apparatus of FIG. 9 operates, according to an exemplary embodiment.

When imaging a plurality of parts of an object while the arm 930 rotates on the stand 940, a distance between the detector 920 and the object may vary, as illustrated in FIG. 13.

FIG. 13 is a diagram illustrating a method in which the X-ray apparatus 900 operates, according to an exemplary embodiment.

As illustrated in FIG. 13, the X-ray apparatus 900 may obtain a plurality of images for a plurality of parts of an object 1303. The X-ray apparatus 900 may determine an imaging section 1306 including a plurality of imaging areas of the object 1303 and obtain a plurality of images while moving a detector 920 to a first position 1311, a second position 1312, and a third position 1313 in the imaging section 1306.

The X-ray apparatus 900 may image a first part of the object 1303 by radiating X-rays from a source 910 toward the detector 920 positioned in the first position 1311 and thus obtain a first image, and may move the detector 920 to the second position 1312 to image a second part of the object in which a portion of the second part overlaps the first part. The X-ray apparatus 900 may image the second part of the object 1303 by radiating X-rays toward the detector 920 positioned in the second position 1312 and thus obtain a second image, and may move the detector 920 to the third position 1313 to image a third part of the object in which a portion of the third part overlaps the second part.

The X-ray apparatus 900 may control the arm 930 so that the arm 930 rotates on the stand 940 to change the position of the detector 920. As the arm 930 rotates on the stand 940, a distance between the detector 920 and the object may vary, as illustrated in FIG. 13. In this case, as the distance between the detector 920 and the object varies, an enlargement ratio of obtained images may vary.

An image 1320 of FIG. 13 is an image obtained by stitching a first image 1321 obtained from the detector 920 positioned in the first position 1311 and a second image 1322 obtained from the detector 920 positioned in the second position 1312. As 'a distance between the detector 920 and the object 1303 when the detector 920 is positioned in the first position 1311' and 'a distance between the detector 920 and the object 1303 when the detector 920 is positioned in the second position 1311' vary, image distortion may occur in an overlapping area 1305 between the first image 1321 and the second image 1322.

In order to correct image distortion occurring since the distance between the detector 920 and the object 1303 varies, the X-ray apparatus 900 may adjust an enlargement or reduction ratio of each of the first and second images 1321 and 1322, based on a distance from the object to the detector 920 when obtaining each of the first and second images 1321 and 1322. The X-ray apparatus 900 may generate a combination image by combining the first and second images 1321 and 1322 each having an adjusted enlargement or reduction ratio.

The X-ray apparatus 900 may control the movement of at least one selected from the source 910, the detector 920, and the arm 930 to correct a variation of the distance between the detector 920 and the object which occurs since the arm 930 rotates on the stand 940.

For example, the X-ray apparatus 900 may move the detector 920 on the arm 930 so that a distance between the object and the detector 920 when obtaining the first image 1321 and a distance between the object and the detector 920 when obtaining the second image 1322 are constant.

The X-ray apparatus 900 may include a driving unit for moving the position of the detector 920 on the arm 930. For example, the driving unit of the detector 920 may include a motor or a gear so that the detector 920 changes a relative position thereof on the arm 930.

For example, the X-ray apparatus 900 may move the detector 920 in a second direction on the arm 930 so that the distance between the object and the detector 920 is constant. The second direction may be a direction perpendicular to the first direction in which the X-ray apparatus 900 divides the object into a plurality of parts, and may be a direction opposite to a direction in which the detector 920 moves based on the object as the arm 930 rotates on the stand 940.

In other words, when the detector 920 becomes more distant from the object as the arm 930 rotates on the stand 940, the X-ray apparatus 900 may move the detector 920 on the arm 930 in a direction in which the detector 920 approaches the object. Alternatively, when the detector 920 approaches the object as the arm 930 rotates on the stand 940, the X-ray apparatus 900 may move the detector 920 on the arm 930 in a direction in which the detector 920 becomes more distant from the object.

As another example, the X-ray apparatus 900 may move the arm 930, centering on the stand 940, for example, centering on the arm connection unit 735 as described above, so that the distance between the object and the detector 920 when obtaining the first image 1321 and the distance between the object and the detector 920 when obtaining the second image 1322 are constant, i.e., maintained the same.

The arm 930 may include a driving unit that moves the position of the arm 930, centering on the stand 940. For example, the driving unit of the arm 930 may include a motor or a gear to change a relative position of the arm 930 on the stand 940.

For example, the X-ray apparatus 900 may move the arm 930 by a first distance in the second direction, centering on the stand 940. The second direction may be a direction perpendicular to the first direction in which the X-ray apparatus 900 divides the object into a plurality of parts, and may be a direction opposite to a direction in which the detector 920 moves based on the object as the arm 930 rotates on the stand 940. The first distance may correspond to a distance by which the detector 920 moves based on the object as the arm 930 rotates on the stand 940.

In other words, when the detector 920 becomes more distant by a first distance from the object as the arm 930 rotates on the stand 940, the X-ray apparatus 900 may move the arm 930, centering on the stand 940, by the first distance in a direction in which the detector 920 approaches the object. Alternatively, when the detector 920 approaches the object by the first distance as the arm 930 rotates on the stand 940, the X-ray apparatus 900 may move the arm 930, centering on the stand 940, by the first distance in a direction in which the detector 920 becomes more distant from the object.

In this case, the X-ray apparatus 900 may move the source 910 in a direction opposite to the second direction along the arm 930 while the X-ray apparatus 900 moves the arm 930, centering on the stand 940. For example, the X-ray apparatus 900 may move the source 910 by the first distance in a direction opposite to the second direction along the arm 930 while the X-ray apparatus 900 moves the arm 930, centering on the stand 940.

The source 910 may include a driving unit that moves the position of the source 910 on the arm 930. For example, the driving unit of the source 910 may include a motor or a gear so that the source 910 changes a relative position thereof on the arm 930.

FIGS. 14 through 17 are diagrams illustrating a method in which the X-ray apparatus 900 operates, according to an exemplary embodiment.

The X-ray apparatus 900 may divide an object into a plurality of parts in a predetermined direction, and may obtain a plurality of images for the plurality of parts of the object by rotating the arm 930, centering on the stand 940, so that detector 920 moves in a predetermined direction. In this case, the X-ray apparatus 900 may control a rotation angle and a moving distance of the arm 930 so that incident angles of X-rays which are incident on an overlapping area between adjacent imaging areas correspond to each other.

Figure 14:
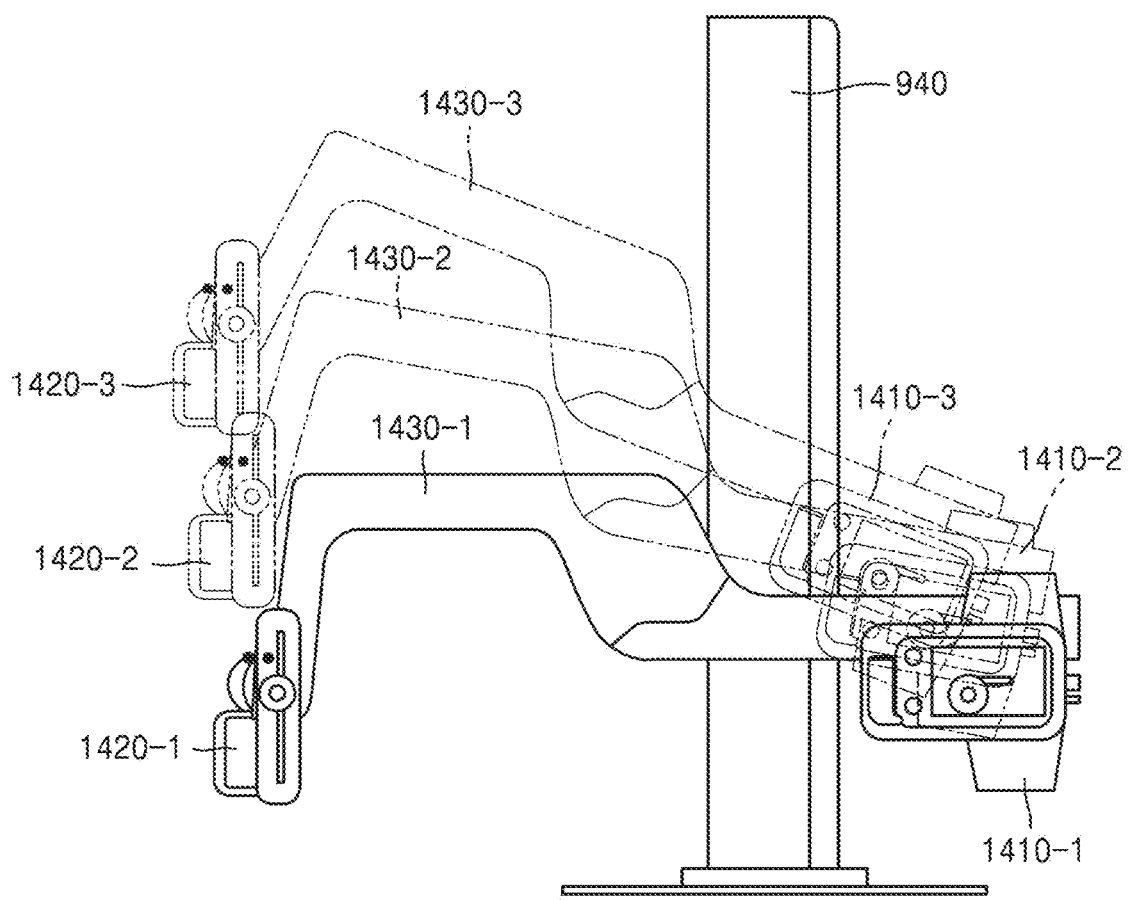
FIGS. 14, 15, 16, and 17 are diagrams illustrating a method in which the X-ray apparatus of FIG. 9 operates, according to an exemplary embodiment.

As illustrated in FIG. 14, the X-ray apparatus 900 may image a first part of the object by radiating X-rays toward the detector 920 positioned in a first position 1420-1 and thus obtain a first image, and may move the detector 920 to a second position 1420-2 to image a second part of the object. Also, the X-ray apparatus 900 may change the position of the source 910 from a first position 1410-1 to a second position 1410-2 so that X-rays are radiated toward the second part of the object.

The X-ray apparatus 900 may move the detector 920 so that the detector 920 positioned in the second position 1420-2 overlaps the detector 920 positioned in the first position 1420-1 by a predetermined section. The X-ray apparatus 900 may control the arm 930 so that the arm 930 rotates by a predetermined angle, to move the source 910 and the detector 920. The X-ray apparatus 900 may determine a distance by which the arm 930 moves along the stand 940, in consideration of the incident angles of the X-rays which are incident on the overlapping area.

The X-ray apparatus 900 may move the arm 930 from a first position 1430-1 to a second position 1430-2 so that an incident angle of X-rays that are incident on an overlapping area between a first part of an object and a second part of the object when obtaining a first image corresponds to an incident angle of X-rays that are incident on an overlapping area between the first part of the object and the second part of the object when obtaining a second image.

The X-ray apparatus 900 may obtain the second image by imaging the second part of the object and move the detector 920 to a third position 1420-3 to image a third part of the object. Also, the X-ray apparatus 900 may change the position of the source 910 from the second position 1410-2 to the third position 1410-3 so that X-rays are radiated toward the third part of the object.

The X-ray apparatus 900 may move the detector 920 so that the detector 920 positioned in the third position 1420-3 overlaps the detector 920 positioned in the second position 1420-2 by a predetermined section. The X-ray apparatus 900 may control the arm 930 so that the arm 930 rotates by a predetermined angle, to move the source 910 and the detector 920. The X-ray apparatus 900 may determine a distance by which the arm 930 moves along the stand 940, in consideration of the incident angles of the X-rays which are incident on the overlapping area.

The X-ray apparatus 900 may move the arm 930 from the second position 1430-2 to the third position 1430-3 so that an incident angle of X-rays that are incident on an overlapping area between the second part of the object and the third part of the object when obtaining the second image is identical to an incident angle of X-rays that are incident on an overlapping area between the second part of the object and the third part of the object when obtaining a third image.

As illustrated in FIG. 14, when a distance between the detector 920 and the object varies as the arm 930 rotates on the stand 940, the X-ray apparatus 900 may adjust an enlargement or reduction ratio of images according to the distance between the detector 920 and the object.

Figure 15:
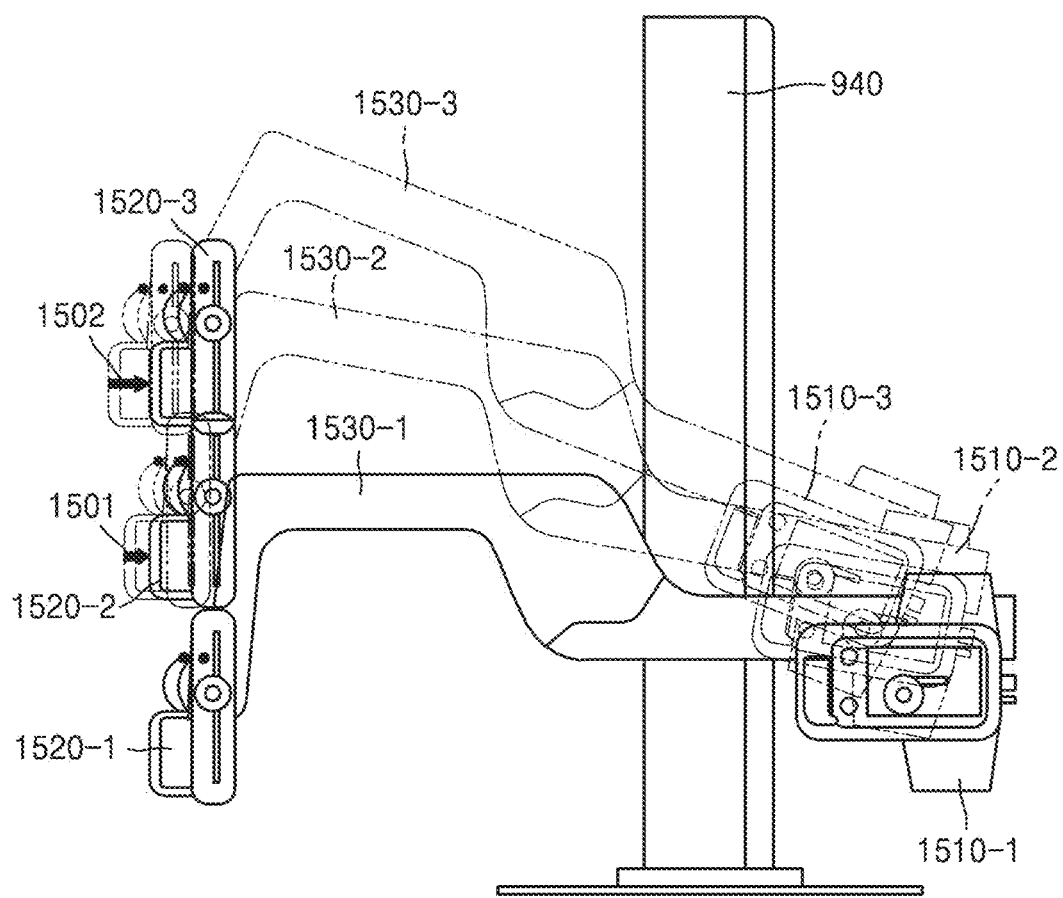

As illustrated in FIG. 15, the X-ray apparatus 900 may move the detector 920 on the arm 930 so that a distance between the detector 920 and an object is constant.

The X-ray apparatus 900 may image a first part of the object by radiating X-rays toward the detector 920 positioned in a first position 1520-1 and thus obtain a first image, and may move the detector 920 to a second position 1520-2 to image a second part of the object. Also, the X-ray apparatus 900 may change the position of the source 910 from a first position 1510-1 to a second position 1510-2 so that X-rays are radiated toward the second part of the object.

The X-ray apparatus 900 may move the detector 920 so that the detector 920 positioned in the second position 1520-2 overlaps the detector 920 positioned in the first position 1520-1 by a predetermined section. The X-ray apparatus 900 may control the arm 930 so that the arm 930 rotates by a predetermined angle, to move the source 910 and the detector 920. The X-ray apparatus 900 may determine a distance by which the arm 930 moves along the stand 940, in consideration of the incident angles of the X-rays which are incident on the overlapping area.

The X-ray apparatus 900 may move the arm 930 from a first position 1530-1 to a second position 1530-2 so that an incident angle of X-rays that are incident on an overlapping area between a first part of an object and a second part of the object when obtaining a first image corresponds to an incident angle of X-rays that are incident on an overlapping area between the first part of the object and the second part of the object when obtaining a second image.

In this case, compared to the second position 1420-2 of the detector 920 illustrated in FIG. 14, the second position 1520-2 of the detector 920 illustrated in FIG. 15 may be a position to which the detector 920 is moved in a direction indicated by an arrow 1501 along the arm 930 so that a distance between the detector 920 and the object is constant. In order to capture the second image after obtaining the first image, the X-ray apparatus 900 may move the detector 920 in the direction indicated by the arrow 1501 along the arm 930 so that the distance between the detector 920 and the object is constant.

The X-ray apparatus 900 may obtain the second image by imaging the second part of the object and move the detector 920 to a third position 1520-3 to image a third part of the object. Also, the X-ray apparatus 900 may change the position of the source 910 from the second position 1510-2 to the third position 1510-3 so that X-rays are radiated toward the third part of the object.

The X-ray apparatus 900 may move the detector 920 so that the detector 920 positioned in the third position 1520-3 overlaps the detector 920 positioned in the second position 1520-2 by a predetermined section. The X-ray apparatus 900 may control the arm 930 so that the arm 930 rotates by a predetermined angle, to move the source 910 and the detector 920. The X-ray apparatus 900 may determine a distance by which the arm 930 moves along the stand 940, in consideration of the incident angles of the X-rays which are incident on the overlapping area.

The X-ray apparatus 900 may move the arm 930 from the second position 1530-2 to the third position 1530-3 so that an incident angle of X-rays that are incident on an overlapping area between the second part of the object and the third part of the object when obtaining the second image corresponds to an incident angle of X-rays that are incident on an overlapping area between the second part of the object and the third part of the object when obtaining a third image.

Compared to the third position 1420-3 of the detector 920 illustrated in FIG. 14, the third position 1520-3 of the detector 920 illustrated in FIG. 15 may be a position to which the detector 920 is moved in a direction indicated by an arrow 1502 along the arm 930 so that the distance between the detector 920 and the object is constant. In order to capture the third image after obtaining the second image, the X-ray apparatus 900 may move the detector 920 in the direction indicated by the arrow 1502 along the arm 930 so that the distance between the detector 920 and the object is constant.

Figure 16:
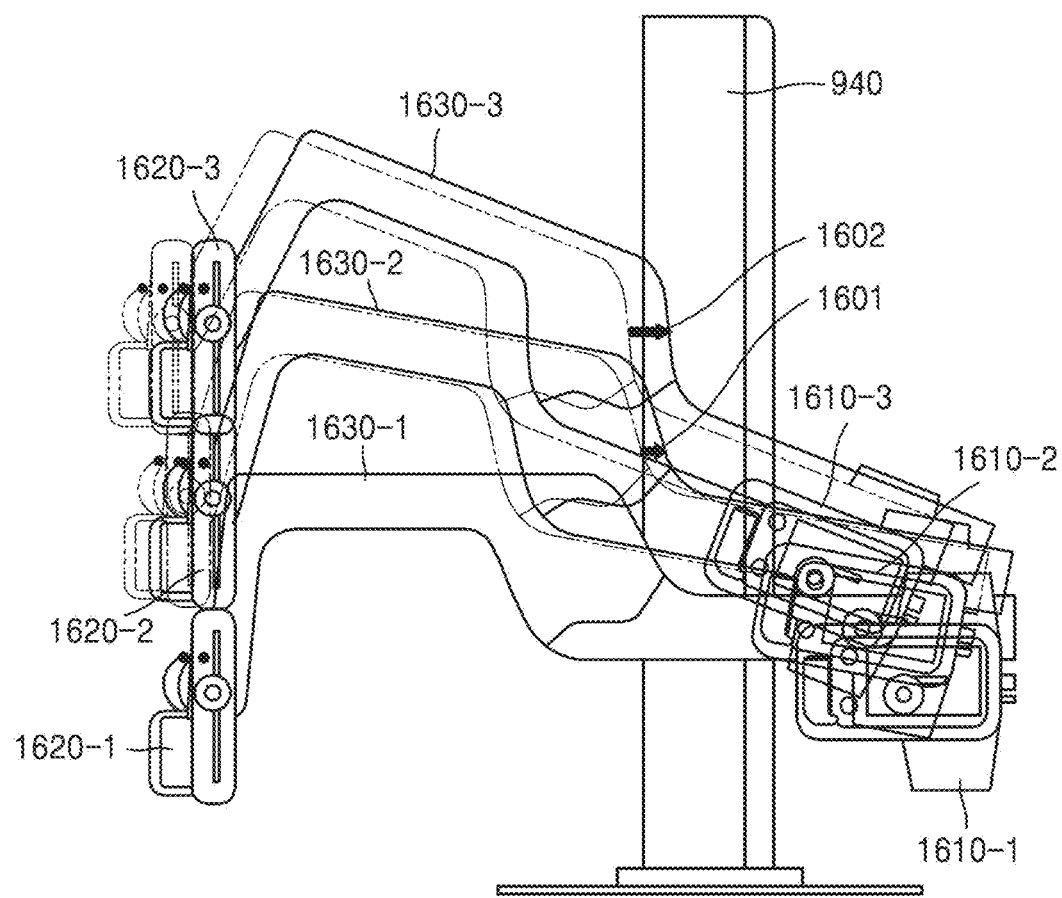

As illustrated in FIG. 16, the X-ray apparatus 900 may move the arm 930, centering on the stand 940, so that a distance between the detector 920 and an object is constant.

The X-ray apparatus 900 may image a first part of the object by radiating X-rays toward the detector 920 positioned in a first position 1620-1 and thus obtain a first image, and may move the detector 920 to a second position 1620-2 to image a second part of the object. Also, the X-ray apparatus 900 may change the position of the source 910 from a first position 1610-1 to a second position 1610-2 so that X-rays are radiated toward the second part of the object.

The X-ray apparatus 900 may move the detector 920 so that the detector 920 positioned in the second position 1620-2 overlaps the detector 920 positioned in the first position 1620-1 by a predetermined section. The X-ray apparatus 900 may control the arm 930 so that the arm 930 rotates by a predetermined angle, to move the source 910 and the detector 920. The X-ray apparatus 900 may determine a distance by which the arm 930 moves along the stand 940, in consideration of the incident angles of the X-rays which are incident on the overlapping area.

The X-ray apparatus 900 may move the arm 930 from a first position 1630-1 to a second position 1630-2 so that an incident angle of X-rays that are incident on an overlapping area between a first part of an object and a second part of the object when obtaining a first image corresponds to an incident angle of X-rays that are incident on an overlapping area between the first part of the object and the second part of the object when obtaining a second image.

In this case, compared to the second position 1420-2 of the detector 920 and the second position 1430-2 of the arm 930, illustrated in FIG. 14, the second position 1620-2 of the detector 920 and the second position 1630-2 of the arm 930, illustrated in FIG. 16, may correspond to a position to which the arm 930 is moved in a direction indicated by an arrow 1601, centering on the stand 940, so that a distance between the detector 920 and the object is constant. In order to capture the second image after obtaining the first image, the X-ray apparatus 900 may move the arm 930 in the direction indicated by the arrow 1501, centering on the stand 940, so that the distance between the detector 920 and the object is constant.

The X-ray apparatus 900 may obtain the second image by imaging the second part of the object and move the detector 920 to a third position 1620-3 to image a third part of the object. Also, the X-ray apparatus 900 may change the position of the source 910 from the second position 1610-2 to the third position 1610-3 so that X-rays are radiated toward the third part of the object.

The X-ray apparatus 900 may move the detector 920 so that the detector 920 positioned in the third position 1620-3 overlaps the detector 920 positioned in the second position 1620-2 by a predetermined section. The X-ray apparatus 900 may control the arm 930 so that the arm 930 rotates by a predetermined angle, to move the source 910 and the detector 920. The X-ray apparatus 900 may determine a distance by which the arm 930 moves along the stand 940, in consideration of the incident angles of the X-rays which are incident on the overlapping area.

The X-ray apparatus 900 may move the arm 930 from the second position 1630-2 to the third position 1630-3 so that an incident angle of X-rays that are incident on an overlapping area between the second part of the object and the third part of the object when obtaining the second image corresponds to an incident angle of X-rays that are incident on an overlapping area between the second part of the object and the third part of the object when obtaining a third image.

Compared to the third position 1420-3 of the detector 920 and the third position 1430-3 of the arm 930, illustrated in FIG. 14, the third position 1620-3 of the detector 920 and the third position 1630-3 of the arm 930, illustrated in FIG. 15, may correspond to a position to which the arm 930 is moved in a direction indicated by an arrow 1602, centering on the stand 940, so that the distance between the detector 920 and the object is constant. In order to capture the third image after obtaining the second image, the X-ray apparatus 900 may move the arm 930 in the direction indicated by the arrow 1602, centering on the stand 940, so that the distance between the detector 920 and the object is constant.

As illustrated in FIG. 16, when the X-ray apparatus 900 moves the arm 930, centering on the stand 940, so that the distance between the detector 920 and the object is constant, the distance between the detector 920 and the object may vary. Accordingly, the X-ray apparatus 900 may move the arm 930 on the source 920 while moving the arm 930 centering on the stand 940.

Figure 17:
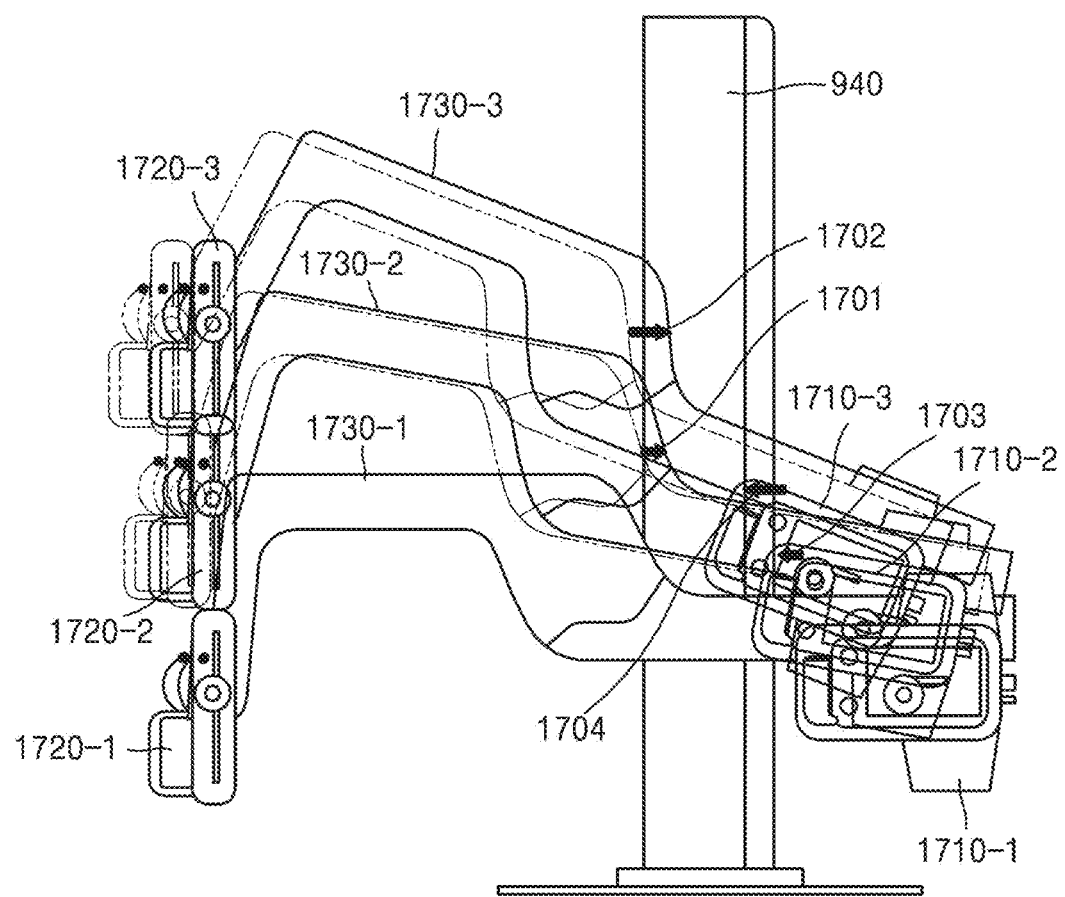

As illustrated in FIG. 17, the X-ray apparatus 900 may image a first part of the object by radiating X-rays toward the detector 920 positioned in a first position 1720-1 and thus obtain a first image, and may move the detector 920 to a second position 1720-2 to image a second part of the object. Also, the X-ray apparatus 900 may change the position of the source 910 from a first position 1710-1 to a second position 1710-2 so that X-rays are radiated toward the second part of the object.

The X-ray apparatus 900 may control the arm 930 so that the arm 930 rotates by a predetermined angle to move the source 910 and the detector 920. In addition, the X-ray apparatus 900 may move the arm 930 from a first position 1730-1 to a second position 1730-2 so that an incident angle of X-rays that are incident on an overlapping area between a first part of an object and a second part of the object when obtaining a first image corresponds to an incident angle of X-rays that are incident on an overlapping area between the first part of the object and the second part of the object when obtaining a second image.

In this case, compared to the second position 1420-2 of the detector 920 and the second position 1430-2 of the arm 930, illustrated in FIG. 14, the second position 1720-2 of the detector 920 and the second position 1730-2 of the arm 930, illustrated in FIG. 17, may correspond to a position to which the arm 930 is moved in a direction indicated by an arrow 1701, centering on the stand 940, so that a distance between the detector 920 and the object is constant. In order to capture the second image after obtaining the first image, the X-ray apparatus 900 may move the arm 930 in the direction indicated by the arrow 1702, centering on the stand 940, so that the distance between the detector 920 and the object is constant. Also, the X-ray apparatus 900 may move the source 910 on the arm 930 in a direction indicated by an arrow 1703 by a moving distance which the arm 930 moves centering on the stand 940.

The X-ray apparatus 900 may obtain the second image by imaging the second part of the object and move the detector 920 to a third position 1620-3 to image a third part of the object. Also, the X-ray apparatus 900 may change the position of the source 910 from the second position 1710-2 to the third position 1710-3 so that X-rays are radiated toward the third part of the object.

The X-ray apparatus 900 may control the arm 930 so that the arm 930 rotates by a predetermined angle to move the source 910 and the detector 920. In addition, the X-ray apparatus 900 may move the arm 930 from the second position 1730-2 to a third position 1730-3 so that an incident angle of X-rays that are incident on an overlapping area between the second part of the object and a third part of the object when obtaining the second image is identical to an incident angle of X-rays that are incident on an overlapping area between the second part of the object and the third part of the object when obtaining a third image.

In this case, compared to the third position 1420-3 of the detector 920 and the third position 1430-3 of the arm 930, illustrated in FIG. 14, the third position 1720-3 of the detector 920 and the third position 1730-3 of the arm 930, illustrated in FIG. 17, may correspond to a position to which the arm 930 is moved in a direction indicated by an arrow 1702, centering on the stand 940, so that a distance between the detector 920 and the object is constant. In order to capture the third image after obtaining the second image, the X-ray apparatus 900 may move the arm 930 in a direction indicated by an arrow 1703, centering on the stand 940, so that the distance between the detector 920 and the object is constant. Also, the X-ray apparatus 900 may move the source 910 on the arm 930 in a direction indicated by an arrow 1704 by a moving distance which the arm 930 moves centering on the stand 940.

As illustrated in FIGS. 15 through 17, the X-ray apparatus 900 may obtain a plurality of images having the same enlargement ratio by maintaining a constant distance between the object and the detector 920 even when a plurality of image are obtained while the arm 930 rotates on the stand 940.

Figure 18:
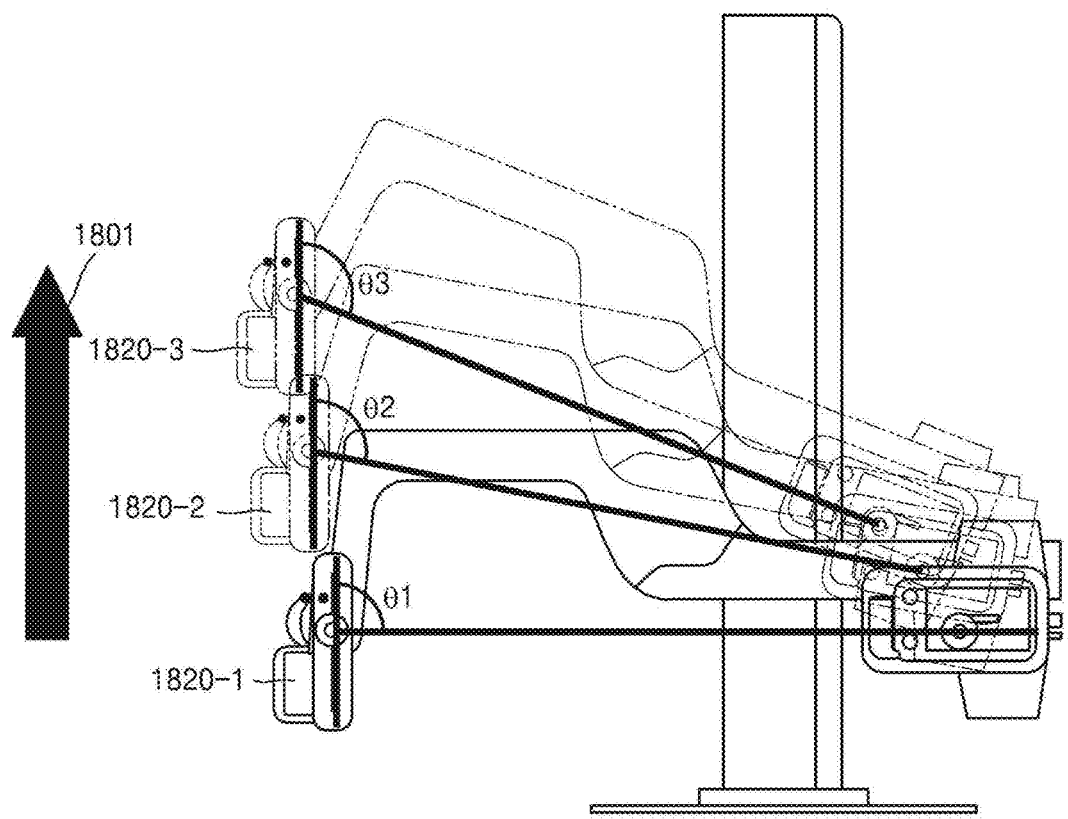
FIGS. 18 and 19 are diagrams illustrating a method in which the X-ray apparatus of FIG. 9 operates, according to an exemplary embodiment.
Figure 19:
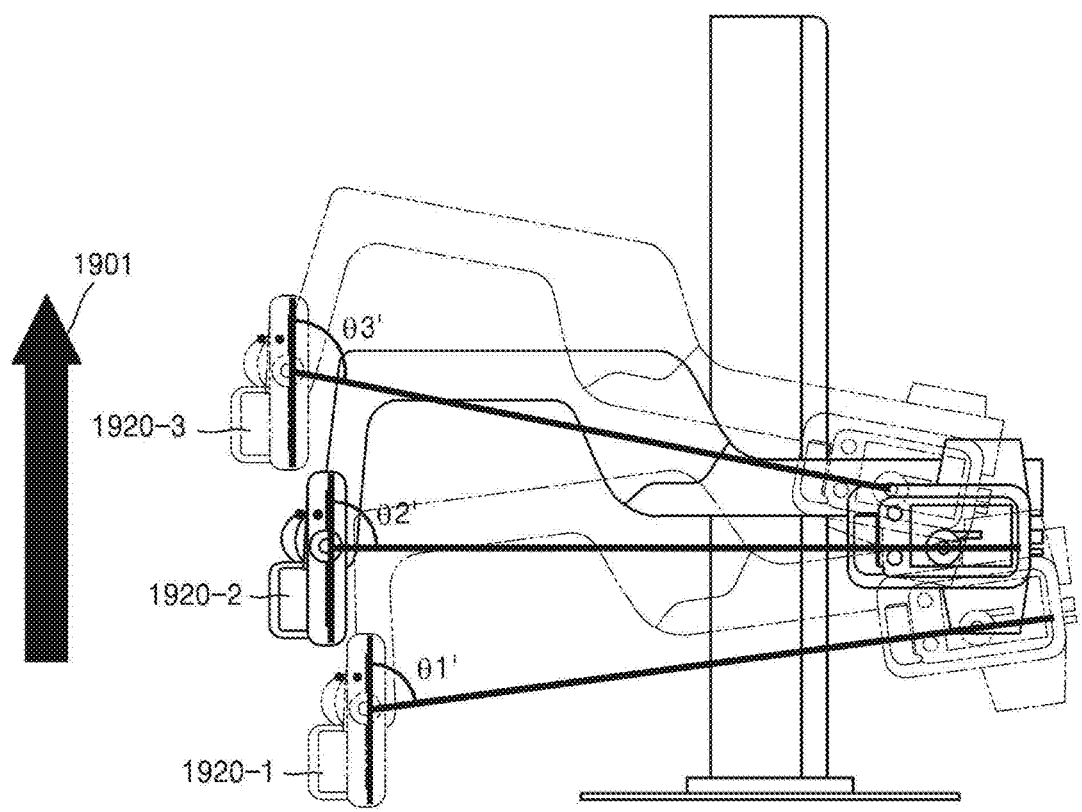

FIGS. 18 and 19 are diagrams illustrating a method in which the X-ray apparatus 900 operates, according to an exemplary embodiment.

As illustrated in FIG. 18, the X-ray apparatus 900 may divide an object into a plurality of parts in a predetermined direction. The X-ray apparatus 900 may move the arm 930 while the arm 930 rotates on the stand 940, so that detector 920 moves from a reference position (that is, a position of the detector 920 when an X-ray radiation angle of the source 910 for an X-ray detection surface of the detector 920 is 90°) toward a direction indicated by an arrow 1801. The X-ray apparatus 900 may obtain images for the plurality of parts of the object by moving the detector 920 from the reference position toward the direction indicated by the arrow 1801. In this case, the X-ray apparatus 900 may control a rotation angle and a moving distance of the arm 930 so that incident angles of X-rays which are incident on an overlapping area between adjacent imaging areas correspond to each other.

The X-ray apparatus 900 may determine a first position 1820-1 as the reference position, obtain a first image for a first part of the object by radiating X-rays toward the detector 920 positioned in the first position 1820-1, and move the detector 920 to a second position 1820-2 to image a second part of the object. The X-ray apparatus 900 may obtain the second image for the second part of the object by radiating X-rays toward the detector 920 positioned in the second position 1820-2 and move the detector 920 to a third position 1820-3 to image a third part of the object. $\Theta 1$, $\Theta 2$, and $\Theta 3$ shown in FIG. 18 denotes X-ray radiation angles of the source 910 in imaging operations performed when the detector 920 is positioned in the first position 1820-1, the second position 1820-2, and the third position 1820-3, respectively.

As illustrated in FIG. 18, when the X-ray apparatus 900 performs a plurality of imaging operations for a plurality of parts of an object, an X-ray radiation angle of the source 910 in a first imaging operation is 90° and an X-ray radiation angle of the source 910 in a second imaging operation is greater than 90°. As the detector 920 moves by a certain distance in a direction indicated by the arrow 1801 to perform a next imaging operation, the X-ray radiation angle of the source 910 may gradually increase. Accordingly, when the number of images to be obtained increases, the X-ray radiation angle of the source 910 may excessively increase.

When the X-ray radiation angle of the source 910 excessively increases, image distortion, in which tissues of the same height are shown as if they are positioned at different heights in an image, may become severe, as shown in FIG. 3A. In particular, when detailed tissues, such as a neck bone, have to be shown, diagnostic accuracy may be lowered due to such image distortion.

Accordingly, the X-ray apparatus 900 may operate as illustrated in FIG. 19.

As illustrated in FIG. 19, the X-ray apparatus 900 may move the arm 930 while the arm 930 rotates on the stand 940, so that the detector 920 moves in a direction indicated by an arrow 1901 while passing a reference position. In this case, the X-ray apparatus 900 may control a rotation angle and a moving distance of the arm 930 so that incident angles of X-rays which are incident on an overlapping area between adjacent imaging areas correspond to each other.

The X-ray apparatus 900 may obtain a first image for a first part of an object by radiating X-rays toward the detector 920 positioned in a first position 1920-1 under the reference position and move the detector 920 to a second position 1920-2 to image a second part of the object. The X-ray apparatus 900 may obtain a second image for the second part of the object by radiating X-rays toward the detector 920 positioned in the second position 1920-2 and move the detector 920 to a third position 1920-3 to image a third part of the object.

The third position 1920-3 may be positioned above the reference position. $\Theta 1'$, $\Theta 2'$, and $\Theta 3'$ shown in FIG. 19 denotes X-ray radiation angles of the source 910 in imaging operations performed when the detector 920 is positioned in the first position 1920-1, the second position 1920-2, and the third position 1920-3, respectively.

As illustrated in FIG. 19, when the X-ray apparatus 900 performs a plurality of imaging operations for a plurality of parts of an object, the X-ray apparatus 900 may control the movement of the arm 930 so that an X-ray radiation angle of the source 910 in a first imaging operation is less than 90° and an X-ray radiation angle of the source 910 in a last imaging operation is greater than 90°. Accordingly, the X-ray apparatus 900 may prevent image distortion occurring due to an excessive increase of the X-ray radiation angle of the source 910.

Although a few exemplary embodiments have been shown and described, exemplary embodiments are not limited thereto. It would be appreciated by those skilled in the art that changes may be made in these exemplary embodi-

What is claimed is:

1. An X-ray apparatus comprising:
a source configured to emit X-rays to an object;
a detector configured to detect the X-rays that have passed through the object;
an arm movably attached to a stand and configured to move the source and the detector for obtaining a plurality of images of respective portions of the object; and
a processor configured to image a first portion of the respective portions of the object, based on the X-rays detected by the detector to obtain a first image of the plurality of images, control the arm to rotate, image a second portion of the respective portions, based on the X-rays detected by the detector to obtain a second image of the plurality of images after the arm has rotated, generate the first image and the second image, adjust an enlargement ratio or a reduction ratio of at least one among the first image and the second image, based on a distance from the object to the detector when imaging each of the first image and the second image, and generate an X-ray stitching image by stitching the first image and the second image, one of the first image and the second image having the adjusted enlargement ratio or the adjusted reduction ratio.

2. The X-ray apparatus of claim 1, wherein the processor is configured to control the source to change an emission direction of the X-rays by controlling a rotation of the arm with respect to the stand.

3. The X-ray apparatus of claim 1, wherein the processor is configured to control the detector to rotate on the arm in an opposite direction with respect to a rotation direction of the arm.

4. The X-ray apparatus of claim 1, wherein, by controlling a rotation of the arm, the processor is configured to control the source to rotate in a same direction as a rotation direction of the arm.

5. An X-ray apparatus comprising:
an arm which has a first part and a second part, and is attached to a stand between the first part and the second part;
a source disposed on the first part of the arm and configured to emit X-rays to an object;
a detector disposed on the second part of the arm and configured to detect the X-rays that have penetrated the object; and
a processor configured to image a first image, of a plurality of images, based on the X-rays detected by the detector for a first portion of respective portions, control the arm to rotate, control the detector to rotate with respect to the arm, and image a second image, of the plurality of images, for a second portion of the respective portions, based on the X-rays detected by the detector, adjust an enlargement ratio of at least one among the first image and the second image, based on a distance from the object to the detector when imaging each of the first image and the second image, and generate a stitching image by stitching the first image and the second image, one of the first image and the second image having the adjusted enlargement ratio.

6. The X-ray apparatus of claim 5, wherein the processor is further configured to control to linearly move the detector toward the source.

7. An X-ray apparatus comprising:
an arm which has a first part and a second part, and is attached to a stand between the first part and the second part;
a source disposed on the first part of the arm and configured to emit X-rays to an object;
a detector disposed on the second part of the arm and configured to detect the X-rays that have penetrated the object, and
a processor configured to image a first image, of a plurality of images, based on the X-rays detected by the detector for a first portion of respective portions, control the arm to rotate, control the detector to rotate with respect to the arm, and image a second image, of the plurality of images, for a second portion of the respective portions, based on the X-rays detected by the detector, adjust a reduction ratio of at least one among the first image and the second image, based on a distance from the object to the detector when imaging each of the first image and the second image, and generate a stitching image by stitching the first image and the second image, one of the first image and the second image having the adjusted reduction ratio.

8. An X-ray apparatus comprising:
a source configured to emit X-rays to an object;
a detector configured to detect the X-rays that have penetrated the object;
an arm configured to connect the source to the detector;
a processor configured to control a rotation of the arm on a stand to change a direction of the X-rays, which are emitted to the object, to move the detector in a first direction, obtain images for a plurality of portions of the object based on the X-rays detected by the detector, adjust an enlargement ratio or a reduction ratio of at least one among the images, based on a distance from the object to the detector when imaging each of the images for the plurality of portions of the object, and generate a stitching image by stitching the images, one of the images having the adjusted enlargement ratio or the adjusted reduction ratio.

9. The X-ray apparatus of claim 8, wherein the images of the plurality of portions comprise a first image of a first portion and a second image of a second portion, and
the processor is configured to control the detector to move along the arm, after obtaining the first image, to obtain the second image.

10. The X-ray apparatus of claim 8, wherein the images of the plurality of portions comprise a first image of a first portion and a second image of a second portion, and
the controller is configured to control the arm to move, after obtaining the first image, by a first distance in a direction perpendicular to a lengthwise dimension of the stand to obtain the second image.

11. The X-ray apparatus of claim 10, wherein the processor is configured to control the source to move by the first distance in a direction opposite to a movement direction of the detector to obtain the second image after obtaining the first image.

12. The X-ray apparatus of claim 8, wherein the images of the plurality of portions comprise a first image of a first portion and a second image of a second portion, and
the controller is configured to control the arm so that the arm rotates based on an incident angle of the X-rays emitted from the source to the detector, to obtain the second image after obtaining the first image.

13. An X-ray imaging method comprising:
capturing a first image of a first portion of an object, by detecting, with a detector, X-rays having been emitted by a source and having been passed through the object;
rotating an arm which supports the source and the detector to change an emission orientation of the source;
rotating the detector on the arm in a direction opposite to a rotation direction of the arm;
capturing a second image of a second portion the object, by detecting the X-rays that have been emitted by the source after the rotating of the arm and the detector;
applying an enlargement ratio or a reduction ratio to at least one among the first image and the second image, based on a distance from the object to the detector when imaging each of the first image and the second image; and
stitching the first image and the second image, one of the first image and the second image having the applied enlargement ratio or the applied reduction ratio.

14. The X-ray method of claim 13, wherein the stitching the first image and the second image comprises:
applying the reduction ratio to one of the first image and the second image, and
stitching the first image with the second image, one of the first image and the second image having the applied reduction ratio.

* * * * *